(12) United States Patent
Knight et al.

(10) Patent No.: US 8,128,984 B2
(45) Date of Patent: Mar. 6, 2012

(54) IMPLANTABLE MATERIAL AND A METHOD FOR THE PREPARATION THEREOF

(75) Inventors: David Philip Knight, Winchester (GB); Nicholas James Vavasour Skaer, Oxford (GB); Andrew Michael Collins, Bristol (GB); Tom Louis Dirk Gheysens, Newbury (GB); Christopher Holland, Oxford (GB)

(73) Assignee: Orthox Limited, Oxfordshire (GB)

( * ) Notice: Subject to any disclaimer, the term of this patent is extended or adjusted under 35 U.S.C. 154(b) by 0 days.

(21) Appl. No.: 12/990,399

(22) PCT Filed: Apr. 30, 2009

(86) PCT No.: PCT/IB2009/051775
§ 371 (c)(1),
(2), (4) Date: Mar. 23, 2011

(87) PCT Pub. No.: WO2009/133532
PCT Pub. Date: Nov. 5, 2009

(65) Prior Publication Data
US 2011/0177151 A1    Jul. 21, 2011

(30) Foreign Application Priority Data
Apr. 30, 2008    (GB) .................................. 0807868.5

(51) Int. Cl.
*A61K 6/083*    (2006.01)
(52) U.S. Cl. ........................................... 427/2.26
(58) Field of Classification Search .................. 427/2.26
See application file for complete search history.

(56) References Cited

U.S. PATENT DOCUMENTS
4,233,212 A * 11/1980 Otoi et al. .................... 530/353

FOREIGN PATENT DOCUMENTS

| | | |
|---|---|---|
| SU | 1535902 | 1/1990 |
| WO | 02/29141 | 4/2002 |
| WO | 02/070550 | 9/2002 |
| WO | 03/022909 | 3/2003 |
| WO | 2004/057068 | 7/2004 |
| WO | 2004/057069 | 7/2004 |
| WO | 2005/012606 | 2/2005 |

OTHER PUBLICATIONS

International Search Report corresponding to International Application No. PCT/IB2009/051775, dated Oct. 2, 2009.
Narayani, "The Coefficients of the Jones-Dole Equation for the Viscosity of Solutions of Potassium Iodide in Mixtures of Water and Dimethylacetamide at 35° C", Australian Journal of Chemistry, vol. 30, 1977, pp. 2303-2305.
Marcus, "Ionic Radii in Aqueous Solutions", Journal of Solution Chemistry, vol. 12, No. 4, 1983, pp. 271-275.

* cited by examiner

*Primary Examiner* — Maryam Monshipouri
(74) *Attorney, Agent, or Firm* — Renner, Otto, Boisselle & Sklar, LLP

(57) ABSTRACT

A method for the preparation of a regenerated silk fibroin solution comprises the steps of: treating silk or silk cocoons with an ionic reagent comprising an aqueous solution of monovalent cations and monovalent anions, the cations and anions having ionic radii of at least 1.05 Angstroms and a Jones-Dole B coefficient of between −0.001 and −0.05 at 25° C.; and subsequently degumming the treated silk or silk cocoons; or alternatively, degumming silk or silk cocoons; and subsequently treating the degummed silk or silk cocoons with an ionic reagent comprising an aqueous solution of monovalent cations and monovalent anions, the cations and anions having ionic radii of at least 1.05 Angstroms and a Jones-Dole B coefficient of between −0.001 and −0.05 at 25° C. The invention also extends to fibroin solution, a fibroin material and an implant useful for cartilage repair.

9 Claims, 9 Drawing Sheets

IMPLANTABLE MATERIAL AND A METHOD FOR THE PREPARATION THEREOF

This application is a national phase of International Application No. PCT/IB2009/051775 filed Apr. 30, 2009 and published in the English language.

FIELD OF THE INVENTION

The present invention relates generally to an implantable material and a method for the preparation thereof. The material is useful, for example, for the replacement, partial replacement, augmentation or repair of damaged articular cartilage, or fibrocartilage of the knee menisci, the temperomandibular joint, the intervertebral disc and articular cartilage of synovial joints.

BACKGROUND OF THE INVENTION

Except where specified below the term fibroin is used to refer generically to the main structural protein of cocoon silks whether they are derived from the domesticated Mulberry Silkworm (*Bombyx mori*) or a transgenic silkworm or from any Wild Silkworm including, but not limited to those producing Muga, Eri or Tussah silks. Furthermore, the term 'silk' is used to refer to the natural fine fibre that silkworms secrete, which comprises the two main proteins, sericin and fibroin, fibroin being the structural fibres in the silk, and sericin being the material surrounding the fibroin and sticking the fibres together in the cocoon. 'Silk cocoon' is used to refer to the casing of silk spun by the larvae of the silk worm for protection during the pupal stage.

Three types of cartilage are found in the body of mammals: white fibrocartilage; yellow elastic cartilage; and hyaline cartilage. Hereafter except where stated, the term cartilage is used in its generic sense including these three different types of cartilage.

White fibrocartilage is found in the menisci of the knee and the tempero-mandibular joint and in intervertebral discs. Yellow elastic cartilage is found in the pinna of the ear, the epiglottis and around the auditory canal. Hyaline cartilage is found mainly as articular cartilage in non-synovial joints where it provides smooth articulating surfaces and in synovial joints where it provides a hard and stiff connective tissue covering the articular surfaces of diarthroidal synovial joints.

Articular hyaline cartilage provides a long lasting, lubricated, low friction joint surface, distributes stresses over a broad area of underlying bone and may help to dissipate shocks during dynamic loading (Mow V C, Ratcliffe A. Structure and function of articular cartilage and meniscus. In: Mow V C, Hayes W C, eds. Basic Orthopaedic Biomechanics. New York: Raven Press, 1991; 143-198). The compressive stiffness of cartilage is extremely important in its function. The stiffness of viscoelastic materials such as cartilage depends greatly on the loading history of the material and the method for measuring it and consequently several moduli are used to describe articular cartilage. For example, Spiller, K. L., Laurencin, S. J., Charlton D, Maher, S. A., Lowman, A. M. (2008) in their paper "Superporous hydrogels for cartilage repair: Evaluation of the morphological and mechanical properties" Acta Biomaterialia 4, 17-25, state that the unconfined compressive elastic modulus of adult articular cartilage is about 1 MegaPascal (MPa), while the aggregate compressive modulus is about 0.33 MPa. Treppo, S. et al. in Comparison of biomechanical and biochemical properties of cartilage from human knee and ankle pairs, Journal of Orthopaedic Research 18, 739-748 (2000), state that the equilibrium modulus of healthy adult human articular cartilage lies between 0.2 and 1.5 MPa with a mean about 0.6 MPa depending on, which joint the cartilage is taken from, the location on the joint and depth. Park, S., Hung, C. T. & Ateshian, G. A. in Mechanical response of bovine articular cartilage under dynamic unconfined compression loading at physiological stress levels, Osteoarthritis and Cartilage 12, 65-73 (2004), state that the unconfined dynamic modulus for bovine tibial cartilage lies between 15-65 MPa depending on applied stress and loading frequency.

The menisci of the knee joint are crescent shaped discs, largely constructed from white fibrocartilage. They are interposed between the femoral condoyle and tibial plateau and have the function of compressive load spreading, shock absorption, stabilization and secretion of synovial fluid for articular lubrication. The structure, function and pathology of the menisci have been reviewed by S. M. Bahgia and M. Weinick, Y. Xing, and K. Gupta (2005) Meniscal Injury, *E-medicine World Library,* 27 Jul. 2005, www.emedicine.com/pmr/topic75.htm. The outer rim is vascular while the central part is avascular fibrocartilage. The menisci contain 70% type I collagen (non-articular cartilage fibrillar collagen). The collagen fibres of the meniscus show a predominantly circumferential orientation together with some radial tie fibres. Collagen orientation is extremely important for the mechanical function and fixation of this structure. Compression of the meniscus leads to tensile hoop loading of the circumferential fibres and radial loading of the radial fibres, resisting spreading and flexing of the menisci. Thus the ability of the meniscus to spread load and dissipate energy is dependent on the integrity of the collagen fibre lay. For this reason damage to these fibres increases the risk of secondary osteoarthrotic damage to the condylar cartilages as the normal load distribution and shock-absorbing functions are impaired.

Meniscal injuries are fairly common in adults and are frequently sports-related. They are less common in children over 10 years old and rare in children under 10 with morphologically normal menisci (Iobst, C. A. and Stanitski, C. L., 2000, Acute knee injuries. Clin Sports Med. 2000 October; 19(4): 621-35).

Total knee replacement involves the insertion of a highly complex metal and polymer implant and cannot be considered as treatment for uncomplicated meniscal injury. The Dacron and Teflon meniscal component may initiate severe synovial reactions (Cook, J. L., Tomlinson, J. L., Kreeger, J. M., and Cook, C. R. 1999. *The American Journal of Sports Medicine* 27:658-665 Induction of meniscal regeneration in dogs using a novel biomaterial) while loosening and mechanical failure are a problem (de Groot, J. H. 1995 Doctoral dissertation. University of Gronigen, Summary p153).

Surgical treatment of damaged menisci is often necessary, for which there are different surgical treatment options.

Small meniscal tears can be repaired directly using sutures, fasteners or arrows. However small tears account for less than <3% of all presented mensical injuries.

Although total or partial removal of the meniscus (meniscectomy) to remove damaged meniscal tissue was popular some forty years ago, it is well understood that this procedure leads to articular cartilage degeneration (King, D. Clin. Orthop. 1990, 252, 4-7; Fairbank, T. J. Journal of Bone and Joint Surgery 1948, 30, 664-670) in turn leading to osteoarthrosis. The extent of the secondary osteoarthrosis caused by menisectomy appears to depend on how much meniscal tissue has been removed. Therefore partial meniscectomy usually involving the removal of about 25-40% of the meniscal tissue is the current most frequently used procedure. However, even with partial mensicectomy, a reduction in both shock absorption and the stability of the knee results in secondary osteoarthrosis in the medium to long-term. Better alternatives to partial meniscectomy are therefore being sort. Allograft transplantation is only partially successful as an alternative to total or partial menisectomy so currently only about 0.1% of meniscal procedures employ this approach. There is no proof that replacement of the meniscus with an allograft can re-establish some of the important meniscal functions, and thereby prevent or reduce the development of osteoarthrosis secondary to meniscectomy (Messner, K. and Gao, J. 1998. The menisci of the knee joint. Anatomical and functional characteristics, and a rationale for clinical treatment. Journal of Anatomy, 193:161-178). The major problems are the lack of remodeling of the graft resulting in inferior structural, biochemical and mechanical properties and insufficient fixation to bone (Messner and Gao 1998, Loc. cit). Further disadvantages include the shortage of suitable donors, difficulties with preservation techniques, the possible transfer of diseases, difficulty in shaping the implant to fit the donor and possible immunological reactions to the implant (Stone, K. R. Clinical Sports Medicine. 1996, 15: 557-571).

In addition to allograft procedures, a number of implantable materials have been suggested as replacements for surgically removed damaged meniscal tissue. These include: collagen treated with pepsin to render it substantially non-immunogenic and subsequently cross-linked with glutaraldehyde; a material made from the submucosa of the small intestine; cross-linked hyaluronic acid, Teflon fibre; carbon fibre; reinforced polyester; and polyurethane-coated Dacron. The mechanical properties of these implant materials are a poor match for those of meniscal fibrocartilage which has an unconfined compressive elastic modulus of about 0.4 to 0.8 MPa. These materials have poor resistance to wear and are not self healing. Some of the above are non-resorbable, and are not replaced by functional tissue in situ. It is therefore not surprising that partial or total meniscal replacements made from collagen, Teflon fibre, carbon fibre, reinforced polyester, or polyurethane-coated Dacron showed high mechanical failure rates (de Groot 1995 loc. cit.). Failure also results from poor fixation and severe inflammatory response (de Groot 1995 loc. cit.).

Elastomers based on amphiphilic urethane block copolymers have been suggested for meniscal repair and tested in an animal model. (Heijkants, R. G. J. C. 2004 Polyurethane scaffolds as meniscus reconstruction materials, Ph.D. Thesis, University of Groningen, The Netherlands, MSC Ph.D.-thesis series 2004-09; ISSN: 1570-1530; ISBN: 90 367 2169 5, chapter 10 pp 167-184). These materials are likely to produce less toxic degradation products than Dacron or Teflon. However, the mechanical properties of the polyurethanes tested did not match native meniscus very well (Heijkants 2004 loc. cit.) and this may help to explain why only poorly orientated collagen was found in the regenerating fibrocartilage in the implanted devices in place of the well-orientated collagen in a normal meniscus. A further potential problem was that the polyurethane materials produced a Stage I inflammatory response (giant cells and some macrophages) (Heijkants 2004 loc. cit.). A follow up study tested a polycaprolactone-polyurethane co-polymer porous meniscal repair device over a two year period. After the testing period the device demonstrated no resorption capability, was not replaced by functional meniscal tissue and demonstrated no prevention of cartilage damage (Welsing R. T. C, van Tienen, T. C., Ramrattan, N., Heijkants, R., Schouten, A. J., Veth, R. P. H. and Buma, P. 2008; Effect on tissue differentiation and articular cartilage degeneration of a polymer meniscal implant: a 2 year follow up study in dogs. Am. Jour. Sports Med. 36 1978-1989).

Recently, tissue engineering strategies for meniscal repair have been suggested including the use of biocompatible scaffolds as a substrate for regeneration, and cellular supplementation to promote remodeling and healing. Little is known, however, about the contributions of these novel repair strategies to the restoration of normal meniscal function (Setton, L. A., Guilak, F, Hsu, E. W. Vail, T. P. 1999 Biomechanical Factors in Tissue Engineered Meniscal Repair. *Clinical Orthopaedics & Related Research*. (367S) supplement: S254-S272, October 1999).

Intervertebral discs lie between the cartilage end caps covering the ends of the vertebral centra. They consist of an outer annulus fibrosus, which surrounds the inner nucleus pulposus. The annulus fibrosus consists of several layers of fibrocartilage. The nucleus pulposus contains loose collagen fibrils and chondrocytes suspended in a mucoprotein gel. Intervetebral discs provide a deformable space between the vertebral bodies which facilitates flexibility of the vertebral column while at the same time acting as a shock absorber (M. D. Humzah And R. W. Soames 1988 "Human Intervertebral Disc: Structure And Function", The Anatomical Record 220: 337-356). Prosthetic discs are used to replace damaged discs in patients with herniated lumbar intervertebral discs, degenerative disc disease in the lumbar region, or post-laminectomy syndrome. They are also used to treat patients with lower back pain refractory to conservative treatment for more than six months and patients currently considered suitable for spinal fusion surgery (NICE guidelines, www.nice.org.uk/guidance/index.jsp?action=byID&r=true &o=11081).

There are significant problems associated with the use of metal-containing and non-metallic prostheses for total disc replacement.

Resilience is an extremely important property for natural meniscal and articular cartilage and for materials used to repair them. Resilience can be defined as the extent to which the material returns to its original thickness after being compressed. More precisely it can be defined as the property of a material to store energy reversibly when it is deformed elastically. In the context of articular and meniscal cartilage it is important as it is a measure of the ability of the material to recover from the deformation caused by the compressive loading produced by standing, walking, running and other movements. The high resilience of meniscal cartilage is also important as it enables it to function as an efficient shock absorber during the repeated loading cycles of walking and running. Resilience can be measured in a number of different ways. Most accurately resilience is the maximum energy per volume that can be elastically stored and is therefore measured by determining the area under the elastic part of the stress-strain curve. The resilience of human articular cartilage measured in this way gave a value of 2.9 $Jm^{-3}$ (Park, S. S., Chi, D. H., Lee, A. S., Taylor, S. R. & Iezzoni 2002, J. C. "Biomechanical properties of tissue-engineered cartilage from human and rabbit chondrocytes" Otolaryngology and head and neck surgery 126, 52-57). However it is simpler to use a measure of the extent to which the deformation is recoverable after one or more loading cycles.

Destruction of the articular cartilage on the articular surfaces resulting in changes to the bone adjacent to the articular cartilage occurs in the condition osteoarthrosis. This commonly affects hip, knee, hands, feet and spinal joints. It causes chronic pain, loss of mobility and often stiffness. Primary osteoarthrosis is mainly an effect of the aging process while secondary osteoarthrosis is caused by changes in the stress distribution in joints resulting from injuries, obesity, ligament degeneration, hardness of the subchondral bone or genetic changes to the joint morphology. Disease states such as diabetes mellitus and gout, and other factors including hormonal changes are also causal in secondary osteoarthrosis. The disease process in primary and secondary osteoarthrosis is the same. Severe osteoarthrosis is commonly treated by insertion of an artificial hip or knee joint prosthesis made from a range of materials including alloy steel, ceramic and synthetic polymers. However, these procedures are expensive and not without risk. In addition, about 4% of total hip replacements fail within 10 years as a result of aseptic loosening, deep infection, prosthesis fracture and other causes. Total knee prostheses in general use have an average rate of failure of about 1% per year while those types of prosthesis less frequently used show failure rates up to 3 times faster. More than one complicated and expensive revision may therefore be required in the lifetime of a young person receiving a total joint replacement. The toxicity of polymeric and metallic wear products is an additional problem. Thus much work has been carried out to find viable alternative procedures to joint replacement for the repair of articular cartilage and hence the prevention and treatment of osteoarthrosis.

Suggested methods for articular cartilage repair can be put into two categories; cell-based and tissue-based methods.

Cell-based methods can be further divided according to whether the cells are implanted with or without incorporation into a matrix and whether the matrix is biodegradable or non-biodegradable. Cell based methods include marrow stimulating techniques, autologous chondrocyte implantation, matrix assisted autologous chondrocyte implantation, and procedures using expanded mesenchymal stem cell cultures. For small focal cartilage lesions cell-based cartilage repair strategies can give better clinical outcomes compared with no treatment. However cell-based strategies cannot be used to treat severe osteoarthrosis and this approach has other problems and limitations (Richter, W. 2007. Cell-based cartilage repair: illusion or solution for osteoarthritis. Current Opinion in Rheumatology 19 (5) 451-456).

Tissue-based methods for articular cartilage repair include autologous perichondrial, periosteal or osteochondral grafts and the implantation of allogenous osteochondral and chondral grafts. There are significant problems and limitations associated with tissue-based methods for articular cartilage repair. For example, autologous osteochondral grafts involve the potentially damaging removal of healthy osteochondral tissue from the joint while problems of allograft procedures include the scarcity of fresh donor material, damage to the graft from immune attack, mechanical deterioration and death of chondrocytes during graft handling and frozen storage and risk of disease transmission. (Hunziker, E. B. 2001 Articular cartilage repair: basic science and clinical progress. A review of the current status and prospects can be found in *Osteoarthritis and Cartilage* (2001) 10, 432-463).

Scaffolds for articular cartilage replacement whether implanted on their own or containing cells, must have appropriate porosity to allow for cell migration and nutrition and mechanical properties similar to those of healthy cartilage to enable load bearing and provide a tough, stiff, low friction articular surface as stated by S. Frenkel and P. D. Cesare, Scaffolds for articular cartilage repair, *Annals of Biomedical Engineering* 32 (1) (2004), pp. 26-34. and by S. J. Hollister, Porous scaffold design for tissue engineering, *Nature Materials* (7) (2006), p. 590. In addition, the scaffold should be capable of rapid remodeling (Hunziker, E. B. (1999) Articular cartilage repair: are the intrinsic biological constraints undermining this process insuperable? *Osteoarthritis and Cartilage* 7, 15-28). Existing methods for repairing articular cartilage suffer from the generic problems of poor mechanical properties, poor tissue integration and chondrocyte loss from the lesion borders while the first of these is the most serious (Hunziker 1999 op. cit.). Scaffolds prepared from synthetic biodegradable polymers such as poly(D,L-lactic-coglycolic acid) (PLGA) generally have good mechanical properties, but are reabsorbed too quickly to give sufficient time for the formation of new tissue. In addition, they generally bind cells poorly as a result of their hydrophobic surfaces and lack of cell adhesion signals. In contrast biological macromolecules generally show better cell binding but poor mechanical properties: Janaár, J. Slovíkovä, A. Amler, E., Krupa, P., et al. Mechanical Response of Porous Scaffolds for Cartilage Engineering. *Physiological. Research.* 56 (*Suppl.* 1): S17-S25, 2007. Existing degradable scaffolds are generally too weak to support the forces found in load bearing cartilage. Spiller, K. L., Laurencin, S. J., Charlton D, Maher, S. A., Lowman, A. M. (2008) Superporous hydrogels for cartilage repair: Evaluation of the morphological and mechanical properties Acta Biomaterialia 4, 17-25. These authors teach the use of non-degradable hydrogel scaffolds prepared from a mixture of the non-degradable polymers poly(vinyl alcohol) and poly(vinyl pyrolidone) incorporating degradable microparticles of poly (lactic-co-glycolic acid). The resulting scaffolds were considerably less stiff (unconfined compressive elastic modulus up to 0.15 MPa; aggregate compressive modulus up to 0.14 MPa) compared with the comparable values of 1 MPa and 0.33 MPa respectively for adult articular cartilage. Thus these scaffolds are neither biodegradable nor comparable to articular cartilage in compressive properties.

U.S. Pat. No. 6,306,169 discloses an implant with a porous macrostructure infiltrated with hydrated polymeric gel. The structure is made from a bioresorbable polymer (poly-L-lactic acid, polycaprolactone, polyhydroxybutarate, or polyanhydrides) and the gel comprises alginate, agarose, carrageenans, glycosaminoglycans, proteoglycans, polyethyelene oxide or collagen monomers.

U.S. Pat. No. 6,514,515, U.S. Pat. No. 6,867,247 and U.S. Pat. No. 7,268,205 disclose a bioresorbable and biocompatible polymer, polyhydroxyalkanoate, for a range of implantable applications including the repair of meniscal and articular cartilage.

De Groot, "Meniscal tissue regeneration in porous 50/50 copoly(L-lactide(epsilon-caprolactone) implants," Biomaterials 18(8):613-22 (1997) discloses the use of porous copoly (L-lactide(epsilon-caprolactone) for meniscal tissue regeneration.

U.S. Pat. No. 6,747,121 discloses the use of a porous resorbable implantable material comprised of a terpopolymer containing L-lactide, a glycolide and one other type of repeat unit selected from the group consisting of D-lactide, D,L-lactide and epsilon-caprolactone.

U.S. Pat. No. 6,103,255 teaches the use of biocompatible and biodegradable polymers for use as components of tissue scaffolds. Such polymers include polycarbonates, polyarylates, block copolymers of polycarbonates with poly(alkylene oxides), block copolymers of polyarylates with poly (alkylene oxides), a-hydroxycarboxylic acids, poly(caprolactones), poly(hydroxybutyrates), polyanhydrides, poly (ortho esters), polyesters and bisphenol-A based poly (phosphoesters).

U.S. Pat. No. 6,679,914 discloses a meniscal prosthesis comprising a plurality of superimposed sheets of animal pericardium cross-linked by an aldehyde. Although the device is likely to be resorbable and may be biocompatible despite the use of aldehyde cross-linking, the patent does not disclose the mechanical properties of the device, which are likely to be considerably inferior to those of the normal meniscus.

CA 2,374,169 discloses a biocompatible, resorbable implantable material for total replacement or reinforcement of connective tissue. The material comprises a flexible elongate tape and a plurality of aligned fibres, the tape comprising two essentially parallel layers of mesh and a hydrogel. The material can be of poly(lactic acid), poly(glycolic acid), polydioxanone, polycaprolactone, polyhydroxybutyrate, poly(trimethylene carbonate) or mixtures of these materials.

Several additional problems and limitations have been noted in synthetic polymer scaffolds in addition to their generally poor match in compressive properties compared with those of cartilage. Polymers containing lactic and/or glycolic acids have been shown to give rise to toxic solutions probably as a result of acidic degradation as described by Tayler M S, Daniels A U, Andriano K P, Heller J (1994) Six bioabsorbable polymers: In vitro acute toxicity of accumulated degradation products. Journal of Applied Biomaterials 5: 151-157. This is of particular concern in connection with cartilage repair in which relatively large quantities of synthetic polymer may be required and where poor vascularity slows the removal of toxic waste products. In addition to lactic and glycolic acid many other biodegradable synthetic polymers contain acidic units including butyric, valeric and caproic acids and it is possible that acidic breakdown products from these may also be toxic. A further concern with poly(lactic) and poly(glycolic) acid is that small particles arise during degradation and these can trigger an inflammatory response as reported by Gibbons D F (1992) "Tissue response to resorbable synthetic polymers". In Degradation Phenomena on Polymeric Biomaterials, Plank H, Dauner M, Renardy M, eds. Springer Verlag, New York. pp 97-104., extensive foreign-body response and osteolytic reactions have been reported in an orthopaedic use of polyglycolic acid as reported by Böstman O, Partio E, Hirvensalo E, Rokannen P (1992), Foreign-body reactions to polyglycolide screws, Acta Orthop Scand 63: 173-176. Similar responses are seen with poly(lactide) as reported by Bergsma E. J., Brujn W, Rozema F. R., Bos R. M., Boering G., Late tissue response to poly(L-lactide) bone plates and screws, Biomaterials 1995; 16(1):25}31. Although biodegradable polyurethanes appear to be satisfactory in in vitro and in vivo trials, urethane monomers are carcinogenic and the long effect of their degradation products and how those products are removed from the body is not clearly understood Gunatillake, P. A. and Adhikari, R. 2003, Biodegradable synthetic polymers for tissue engineering, European Cells and Materials, 5.1-16.

WO 2005/094911 discloses a composite material comprising one or more silk elements in an acrylic or cross-linked protein matrix. The material can be used in a wide range of implantable devices and can be made from certain Wild silks naturally decorated with the integrin-binding tripeptide RGD. This tripeptide in Wild silks may facilitate the binding of mesenchymal and other cells. The material was prepared according to the standard protocol described for example by Chen, X., Knight, D. P., Shao, Z. Z., and Vollrath, F. (2001) "Regenerated Bombyx silk solutions studied with rheometry and FTIR" Polymer, 42, 9969-9974. The document reports that the standard protocol results in considerable degradation of the fibroin, which would yield scaffolds with reduced strength, stiffness and resilience.

The standard protocol for preparing regenerated fibroin solutions involves degumming in hot alkaline solutions and dissolution in hot 9M to 9.5M lithium bromide solution. Recently, it has been suggested that cartilage-like materials prepared in vitro by culturing sponges made of regenerated silk fibroin inoculated with chondrocytes or mesenchymal stem cells may have potential for cartilage repair as reviewed by Hofmann S, Knecht S, Langer R, Kaplan D L, Vunjak-Novakovic G, Merkle H P, Meinel L: "Cartilage-like tissue engineering using silk scaffolds and mesenchymal stem cells". Tissue Engineering 2006, 12(10):2729-2738 and by Vepari C, Kaplan DL: "Silk as a biomaterial". Progress in Polymer Science (Oxford) 2007, 32(8-9):991-1007. Little work however appears to have been done to characterize the mechanical properties of fibroin scaffolds which appear to be considerably less stiff, less strong and with higher friction surfaces than adult articular cartilage. However, three papers by Morita's group describe an initial attempt to define the effect of time in culture on the compressive properties of a potential cartilage replacement material grown in vitro by seeding a porous fibroin sponge with chondrocytes. This group showed that the dynamic compressive modulus in this material decreased with time while creep deformation increased with longer cultivation as disclosed by Morita Y, Ikeuchi K, Tomita N, Aoki H, Suguro T, Wakitani S, Tamada Y: "Evaluation of dynamic visco-elastic properties during cartilage regenerating process in vitro". Bio-medical materials and engineering 2003, 13(4):345-353 and the same authors in "Visco-elastic properties of cartilage tissue regenerated with fibroin sponge", Bio-Medical Materials and Engineering 2002, 12(3):291-298. In addition, the coefficient of friction of the surface of a potential cartilage replacement material grown in vitro by seeding a porous fibroin sponge with chondrocytes was initially as low as that of natural cartilage but increased with increasing duration of a sliding test as a result of exudation of interstitial water from the surface layer as disclosed by Morita Y, Tomita N, Aoki H, Sonobe M, Suguro T, Wakitani S, Tamada Y, Ikeuchi K in their paper entitled, "Frictional properties of regenerated cartilage in vitro". Journal of Biomechanics 2006, 39(1):103-109.

WO 2007/020449 discloses an implantable cartilaginous meniscal repair device partly or wholly comprised of porous fibroin. The regenerated fibroin used was prepared using the standard protocol resulting in a scaffold with reduced strength, stiffness and resilience.

WO 2004/US00255, US 20040107 and US 2007/0187862 disclose methods for producing porous silk fibroin scaffold material. A regenerated silk fibroin is first prepared converted to a porous fibroin scaffold using either salt leaching or gas foaming followed in both cases by treatment with methanol or propanol to stiffen and strengthen the material. The material is intended for use as a scaffold for growing a cartilage-like material in vitro. The protocol used for the preparation of the fibroin solution described in US 2007/0187862 involves degumming by boiling cocoons for 20 minutes in an aqueous solution of 0.02 M sodium carbonate solution followed by dissolution of the fibroin in 9.3 M lithium bromide at 60° C. Thus the protocol they used is closely similar to the standard protocol described in the literature and to that used by Holland, C., Terry, A. E., Porter, D. & Vollrath, F. in their paper "Natural and unnatural silks", Polymer 48, 3388-3392 (2007). The latter authors prepared a regenerated fibroin solution prepared according to the standard protocol and compared the rheology of this and native Bombyx mori silk fibroin solution taken directly from the silk gland of the silkworm and at the same protein concentration. They concluded that the vast reduction of viscosities and storage modulus values they observed in the regenerated silk fibroin could be explained by degradation of both molecular weight and folding of the fibroin as a consequence of the protocol used. Thus there is strong evidence that the conditions for preparing the fibroin solution disclosed in US 2007/0187862 produce a marked degradation of the fibroin. This is likely to have a markedly negative impact on the compressive strength, moduli and resilience of the porous material produced from the silk fibroin solution.

WO 2007/020449 teaches an implantable cartilage repair device comprised of a three dimensional biomimetic fibrelay and a bioresorbable porous hydrogel. The hydrogel can be at least partially comprised of regenerated fibroin. The fibroin for the preparation of the porous hydrogel is prepared using the standard protocol comprising the steps of dissolving degummed silk in hot 9.3M lithium bromide solution; dialyzing resulting solution exhaustively against deionised water for two days and concentrating it in a vacuum dessicator.

US 2005/0281859 describes a method of forming an object from a feedstock, such as fibroin, capable of undergoing a sol-gel transition by adjusting the conditions to cause the feedstock to flow and then adjusting the conditions to gel the feedstock.

It has recently been shown that porous fibroin hydrogels prepared from the standard protocol are weak and have reduced resilience. Thus, there is still scope for improvement in the implantable materials and implants used for the replacement, partial replacement, or augmentation, or repair of damaged cartilage.

It is therefore, an object of the present invention to provide an improved regenerated fibroin solution and method of preparing an improved regenerated fibroin solution.

Another object of the invention is to provide an implantable fibroin material and a method of preparing the fibroin material, having improved mechanical properties.

It is a further object of the invention to provide an implant for the total or partial replacement, augmentation or repair of cartilage.

SUMMARY OF THE INVENTION

According to a first aspect of the invention, there is provided a method of preparing a regenerated fibroin solution, the method comprising steps of:
  treating silk or silk cocoons with an ionic reagent comprising an aqueous solution of monovalent cations and monovalent anions, the cations and anions having ionic radii of at least 1.05 Angstroms and a Jones-Dole B coefficient of between −0.001 and −0.05 at 25° C.; and
  subsequently degumming the treated silk or silk cocoons; or alternatively
  degumming silk or silk cocoons; and
  subsequently treating the degummed silk or silk cocoons with an ionic reagent comprising an aqueous solution of monovalent cations and monovalent anions, the cations and anions having ionic radii of at least 1.05 Angstroms and a Jones-Dole B coefficient of between −0.001 and −0.05 at 25° C.

As will be readily understood by those skilled in the art, the B coefficient of the Jones-Dole equation (Jones, G., and Dole, M., *J. Am. Chem. Soc.*, 1929, 51, 2950) is related to the interaction between ions and water and is interpreted as a measure of the structure forming and structure-breaking capacity of an electrolyte in solution.

Preferably, the cations and anions have a Jones-Dole B coefficient of between −0.001 and −0.046 at 25° C.

More preferably, the cations and anions have a Jones-Dole B coefficient of between −0.001 and −0.007 at 25° C.

It is particularly preferred that the method comprises a further step of drying the silk or silk cocoons after treatment of the silk or silk cocoons with the ionic reagent. Preferably, the drying step is performed consecutively after the step of treatment with the ionic reagent.

The aim of the drying step is to extract as much water as possible from the treated silk or silk cocoons. Ideally, substantially all of the water is removed from the treated silk or silk cocoons The process of drying the silk or silk cocoons may be performed by any suitable means, such as, for example, air drying, freeze drying, or drying through the application of heat.

Preferably, the step of drying the silk or silk cocoons comprises air drying.

The silk or silk cocoons may be dried at any suitable temperature. For instance, good results have been observed by drying the silk or silk cocoons at room temperature (21° C.).

The silk or silk cocoons may be dried over any suitable time period. Typically, the silk or silk cocoons may be dried for a period of several hours, for example 12-16 hours.

In some embodiments, the silk or silk cocoons may be air dried in conditions of less than 20% humidity. Preferably, drying of the silk or silk cocoons is carried out in the presence of a desiccant, which may include anhydrous calcium chloride or other suitable desiccant. Other suitable desiccants may include silica gel, calcium sulfate, calcium chloride, and montmorillonite clay. Molecular sieves may also be used as desiccants.

The ionic reagent may comprise a hydroxide solution. The hydroxide solution may be formed in situ. For example, the silk or silk cocoons may be treated with ammonia gas or vapour to form ammonium hydroxide in combination with water already present in the silk or silk cocoons. Further, water vapour may be added to the silk or silk cocoons either before the ammonia gas or vapour, with the ammonia gas or vapour or subsequently.

Suitable ionic reagents include aqueous solutions of ammonium hydroxide, ammonium chloride, ammonium bromide, ammonium nitrate, potassium hydroxide, potassium chloride, potassium bromide or potassium nitrate.

The ionic reagent functions to increase the solubility of proteins in the silk by increasing the charge density on the protein ('salting in').

According to a second aspect of the invention, there is provided a method of preparing a regenerated fibroin solution, the method comprising steps of:
  treating silk or silk cocoons with an ionic reagent comprising an aqueous solution of monovalent cations and monovalent anions, wherein the cations are selected from any one or more of the following: ammonium, potassium, rubidium, and the anions are selected from one or more of the following: hydroxide, chloride, bromide, nitrate; and
  degumming the treated silk or silk cocoons; or alternatively
  degumming silk or silk cocoons; and
  treating the degummed silk or silk cocoons with an ionic reagent comprising an aqueous solution of monovalent cations and monovalent anions, wherein the cations are selected from any one or more of the following: ammonium, potassium, rubidium, and the anions are selected from one or more of the following: hydroxide, chloride, bromide, nitrate.

It will be appreciated that the preferred features described in relation to the first aspect of the invention apply to the second aspect of the invention.

The methods may comprise a subsequent step (c) of dissolving the degummed silk or silk cocoons in a chaotropic agent.

The step of dissolving the silk or silk cocoons may be performed under any one of the following conditions, or any combination of the following conditions:

at a temperature of less than 60° C.;
    with a concentration of chaotropic agent up to 9.5M; and
    for a period of time of less than 24 hours.

The degummed silk or silk cocoons may be dissolved in the chaotropic agent at any suitable temperature, for example, within a temperature range of approximately 10° C. to approximately 60° C. For instance, the degummed silk or silk cocoons are dissolved in the chaotropic agent within a temperature range of approximately 15° C. to approximately 40° C. By way of example, good results have been achieved by dissolving the degummed silk or silk cocoons in the chaotropic agent at a temperature of approximately 37° C.

The degummed silk or silk cocoons may be dissolved in the chaotropic agent at any suitable concentration, for example, in a concentration of the chaotropic agent of 9.3M. For instance, the degummed silk or silk cocoons may be dissolved in a concentration of the chaotropic agent of less than 9M. The degummed silk or silk cocoons may be dissolved in a concentration of the chaotropic agent within the concentration range of approximately 7M to approximately 9M.

The degummed silk or silk cocoons may be dissolved in the chaotropic agent for any suitable time period, for example, a time period of less than 24 hours.

In another aspect of the invention, there is provided a method of preparing a regenerated fibroin solution, the method comprising the steps of:

(a) treating silk or silk cocoons with an ionic reagent comprising an aqueous solution of monovalent cations and monovalent anions, the cations and anions having ionic radii of at least 1.05 Angstroms and a Jones-Dole B coefficient of between −0.001 and −0.05 at 25° C.; and
    (b) subsequently dissolving the silk or silk cocoons in a chaotropic agent, wherein the step of dissolving the silk or silk cocoons is performed under any one of the following conditions, or any combination of the following conditions:

at a temperature of less than 60° C.;
    with a concentration of chaotropic agent less than 9M; and
    for a period of time of less than 24 hours.

The method may comprise a further step of degumming the silk or silk cocoons, preferably before dissolving the silk or silk cocoons in the chaotropic agent.

The degumming step may be performed before step (a). Alternatively, the degumming step may be performed after step (a). Alternatively still, the degumming step may be performed at the same time as step (a).

The degummed silk or silk cocoons may be dissolved in the chaotropic agent within a temperature range of approximately 10° C. to approximately 60° C. Preferably, the degummed silk or silk cocoons are dissolved in the chaotropic agent within a temperature range of approximately 15° C. to approximately 40° C. By way of example, particularly good results have been achieved where the degummed silk or silk cocoons are dissolved in the chaotropic agent at a temperature of approximately 37° C.

Preferably, the degummed silk or silk cocoons are dissolved in the chaotropic agent at a concentration of chaotropic agent within the range of approximately 6M to 9M, for example, approximately 7M.

Preferably, the degummed silk or silk cocoons are dissolved in the chaotropic agent for a period of time of less than 12 hours. Most preferably, the degummed silk or silk cocoons are dissolved in the chaotropic agent for a period of time of less than 4 hours.

The chaotropic agent may comprise one suitable chaotropic agent or a combination of suitable chaotropic agents. Suitable chaotropic agents include lithium bromide, lithium thiocyanate, or guanidinium thiocyanate. A preferred the chaotropic agent comprises an aqueous lithium bromide solution.

In one preferred embodiment, the step of dissolving may be performed at a temperature of approximately 60° C. with a concentration of approximately 9.3 M lithium bromide solution for approximately 2 hours. Alternatively, the step of dissolving may be performed at a temperature of approximately 60° C. with a concentration of approximately 7 M lithium bromide solution for a period of approximately 6 hours. As a further alternative, the step of dissolving may be performed at a temperature of approximately 20° C. with a concentration of approximately 9.3 M lithium bromide solution for a period of approximately 24 hours. Most preferably the step of dissolving is performed at a temperature of approximately 37° C. with a concentration of approximately 9.3M lithium bromide solution for a period of approximately 4 hours.

Degumming the silk or silk cocoons may comprise the selective removal of sericin from the silk or silk cocoons and may use a proteolytic enzyme which cleaves sericin, but produces little or no cleavage of fibroin. The proteolytic enzyme may comprise trypsin. Alternatively, the proteolytic enzyme may comprise proline endopeptidase. Degumming may use an enzyme solution in a buffer containing ammonium hydroxide.

Degumming may be performed at any suitable temperature, for example, a temperature of less than 100° C. Preferably, degumming is performed at a temperature in the range of approximately 20° C. to approximately 40° C. Good results have been observed where degumming is performed at a temperature of approximately 37° C.

The chaotropic agent may be removed by dialysis to provide a regenerated silk fibroin solution. For example, dialysis may be performed using high grade deionised grade II water and is typically carried out using ultrapure grade I water ultrapure water.

Dialysis may be performed at any suitable temperature, for example within a temperature range of approximately 0° C. to approximately 40° C., more preferably in a temperature range of approximately 2° C. to approximately 10° C. Good results have been achieved at a temperature of approximately 4° C.

The method may comprise the step of concentrating the regenerated silk fibroin solution. The solution may be concentrated by exposing sealed dialysis tubes to a vacuum. The regenerated silk fibroin solution may be concentrated to a concentration of approximately 5-25% w/v. Preferably, the regenerated silk fibroin solution is concentrated to a concentration of approximately 8-22% w/v. More preferably, the regenerated silk fibroin solution is concentrated to a concentration of approximately 8-12% w/v. By way of example, particularly good results have been achieved where the regenerated silk fibroin solution is concentrated to a concentration of approximately 10% w/v.

In a further aspect of the invention, there is provided a regenerated silk fibroin solution obtainable by any of the methods according to the aspects of the invention as described herein.

Another aspect of the invention provides a method of preparing a fibroin material comprising gelling the regenerated silk fibroin solution described herein.

The regenerated silk fibroin solution may be gelled, for example, by subjecting the solution to microwave radiation, sound, infra-sound or ultrasound, laser radiation or mechanical shearing or rapid extensional flow.

As a preferred option, the regenerated silk fibroin solution is gelled by treating the fibroin solution with an aqueous solution of one or more gelling reagents, such as, for example, an acid. The acid may be an acidic solution or acidic buffer or acidic vapour. By way of example, particularly good results have been achieved using a gelling agent comprising an acetic acid solution. The acetic acid solution may comprise glacial acetic acid vapour.

The regenerated silk fibroin solution may be gelled to form a hydrogel.

Gellation may be performed at any suitable temperature, for example, within a temperature range of approximately 0° C. to approximately 30° C. for a period of, for example, approximately 4 hours, where gellation is performed on a 10 mm diameter sample in a Visking tube with a 1% solution of acetic acid surrounding the tube.

In a preferred embodiment, gellation is performed at a temperature of approximately 20° C. using a 1% solution of acetic acid for a period of time determined by the depth of penetration of the gellation required calculated on the basis of penetration rate of 18 microns per minute, or approximately 1 mm per hour.

The regenerated silk fibroin solution may be transferred to a mould for gelling. The mould may have a polished surface.

The gelled material may be subjected to one or more freezing cycles. Freezing may be performed at any suitable temperature, for example, within a temperature range of approximately −1° C. to approximately −120° C. Preferably, freezing is performed within a temperature range of approximately −10° C. to approximately −30° C. For example, good results have been achieved where freezing is performed at a temperature of approximately −14° C.

Freezing of the gelled material may comprise zone freezing.

A further aspect of the invention provides a fibroin material obtainable by any one of the methods described herein.

An aspect of the invention provides an implantable cartilage replacement material comprising essentially of silk fibroin, the material having load bearing capacity comprising compressive strength and compressive toughness approximately matching that of cartilage at the site of implantation to enable it to maintain its mechanical integrity without undue distortion when subjected to the forces applied to it by normal physical activity.

According to another aspect of the invention, there is provided an implantable fibroin material, the material comprising the following properties: an unconfined compressive tangent modulus of between 0.3-5.0 MPa at 5% strain; an ultimate compressive strength (stress to yield point) of 1-20 MPa; an average cumulative non-recoverable deformation of less than 10% after 3 million cycles to a nominal strain of 5% in phosphate buffered saline; and a Dynamic Modulus of at least 1.5 MPa after at least 3 million cycles to a nominal strain of 5% in phosphate buffered saline.

The material may comprise an unconfined compressive tangent modulus of approximately 1 MPa to approximately 4.0 MPa at 5% strain. Preferably, the material comprises an unconfined compressive tangent modulus of approximately 1.2 MPa to approximately 1.8 MPa at 5% strain.

The material may comprise an ultimate compressive strength (stress to yield point) of approximately 3 MPa to approximately 9 MPa. Preferably, the material comprises an ultimate compressive strength (stress to yield point) of approximately 4 MPa to approximately 6 MPa.

The material may comprise an average cumulative non-recoverable deformation of less than 10% after 3 million cycles to a nominal strain of 5% in phosphate buffered saline.

Preferably, the material further comprises intercommunicating pores.

The pores may cover from approximately 10% up to approximately 80% of a cross-section of the material. In a preferred embodiment, the pores cover approximately 75% of a cross-section of the material.

The pores may range from approximately 10 µm to approximately 1000 µm in diameter. The average pore diameter may range from approximately 200 µm to approximately 400 µm.

The material may be biocompatible and at least partially bioresorbable. A loss of material may be seen after 12 months of implantation.

The material may have a smooth articular surface whose local stiffness exceeds that of the bulk stiffness by at least 10% and up to approximately 100% as measured by an indenter. The surface may incorporate substances to lower the coefficient of friction when wet, such as, for example only, substances including lubricin.

Preferably, the fibroin is radially orientated in the pore walls.

According to a further aspect of the invention, there is provided an implant for the replacement, partial replacement, augmentation or repair of articular cartilage or fibrocartilage comprising the fibroin material described herein, including the fibroin material prepared by any one of the methods described herein.

According to another aspect of the invention there is provided use of an ionic reagent comprising an aqueous solution of monovalent cations and monovalent anions, the cations and anions having ionic radii of at least 1.3 Angstroms and a Jones-Dole B coefficient of between −0.05 and +0.1 at 25° C. to improve the solubility of silk or silk cocoons in a chaotropic agent.

The ionic reagent may be selected from any one or more of the following: ammonium, potassium, rubidium, and the anions may be selected from one or more of the following: hydroxide, chloride, bromide, nitrate.

There is also provided an implantable material comprised substantially or wholly from protein the implantable material having the following combination of properties: stiff, with an unconfined compressive tangent modulus of between 0.3-5.0 MPa at 10% strain; strong, with an ultimate compressive strength (stress to yield point) of up to 1-20 MPa; resilient, where the material shows average cumulative non-recoverable deformation less than 2% after five 2-minute loading cycles of up to 12% strain; porous, with intercommunicating pores of an average size ranging from 20 to 1000 µm; and resorbable, showing substantial loss of protein as demonstrated by histological staining after 12 months of implantation into a knee joint.

Preferably, the protein is fibroin.

Furthermore, there is provided a method of preparing an optimised regenerated fibroin solution using mild conditions for degumming the silk or silk cocoons and for dissolving the fibroin in a chaotropic agent.

Preferably, drops of the fibroin solution at a concentration of approximately 5-25% w/v have a gellation time of less than 5 minutes at approximately 20° C. when exposed to glacial acetic acid vapour.

Preferably, the optimised regenerated fibroin solution is capable of forming a mesophase. Preferably, the optimised regenerated fibroin solution at a concentration of approximately 18-22% w/v has a viscosity of at least $10^3$ Pa·s at a shear rate of 0.1/s and a G prime modulus of at least $10^2$ Pa at an angular frequency of 10 rad/s at 25° C. as measured by a 10 mm diameter cone and plate geometry with a 1° incline.

Preferably, the material is gelled and then frozen to produce a porous material.

According to a further aspect of the invention there is provided a process for preparing a partially or substantially porous, resorbable material comprising the steps of: treating the silk or silk cocoons with ammonia or an aqueous solution containing ammonium ions; enzymatically degumming the silk or silk cocoons; dissolving the silk or silk cocoons in aqueous lithium bromide solutions at reduced temperature and/or at reduced lithium bromide concentration or in other chaotropic agents; removing the chaotropic agent by dialysis against ultrapure water in the cold; concentrating the solution; transferring the solution to a mould; converting the solution to a hydrogel; subjecting the hydrogel to one or more freezing cycles; and optionally air drying or freeze drying the hydrogel.

According to another aspect of the invention there is provided a process to form stiff, strong and tough porous materials from fibroin comprising the steps of: treating the silk or silk cocoons with ammonia or an aqueous solution containing ammonium ions; degumming the silk or silk cocoons with an enzyme under mild conditions; dissolving the silk or silk cocoons in aqueous lithium bromide solutions at reduced temperature and/or at reduced lithium bromide concentration and/or for shorter times or in other chaotropic agents; removing the chaotropic agent by dialysis against ultrapure water in the cold; optionally concentrating the solution; transferring the solution to a mould; gelling the solution by treating it with an acid, for example, an acidic solution or acidic buffer or acidic vapour, or other means; and subjecting the gel to one or more freezing cycles; optionally treating the resultant scaffold with an aqueous ethanol solution; optionally freeze drying the scaffold; and optionally cross-linking the scaffold with a cross-linking agent.

With the abovementioned methods, the resulting material has a highly porous interconnected pore structure with an average pore size of 20 µm to 1 mm and unconfined compressive elastic moduli from 0.3 to 5 MPa. The material may be provided with a stiff and smooth coat by casting it on a polished surface.

Other objects, features and advantages of the invention will be apparent from the following detailed disclosure, taken in conjunction with the accompanying figures.

DETAILED DESCRIPTION OF THE INVENTION

Where mentioned below, the terms 'optimised regenerated fibroin' and 'optimised regenerated silk fibroin' are used to refer to materials comprising fibroin that have been obtained as a result of the methods according to the invention.

The implantable optimised fibroin material according to an exemplary embodiment of the present invention is comprised essentially of regenerated silk fibroin. The material has shown high open porosity in addition to improved stiffness, viscoelasticity and resilience over the course of prolonged compression testing when compared with standard fibroin materials. The material comprises a smooth, stiff and tough surface providing a low friction surface when lubricated with synovial fluid. The material has also demonstrated resorbability, biocompatibility and good adhesiveness for cells.

Figure 1:
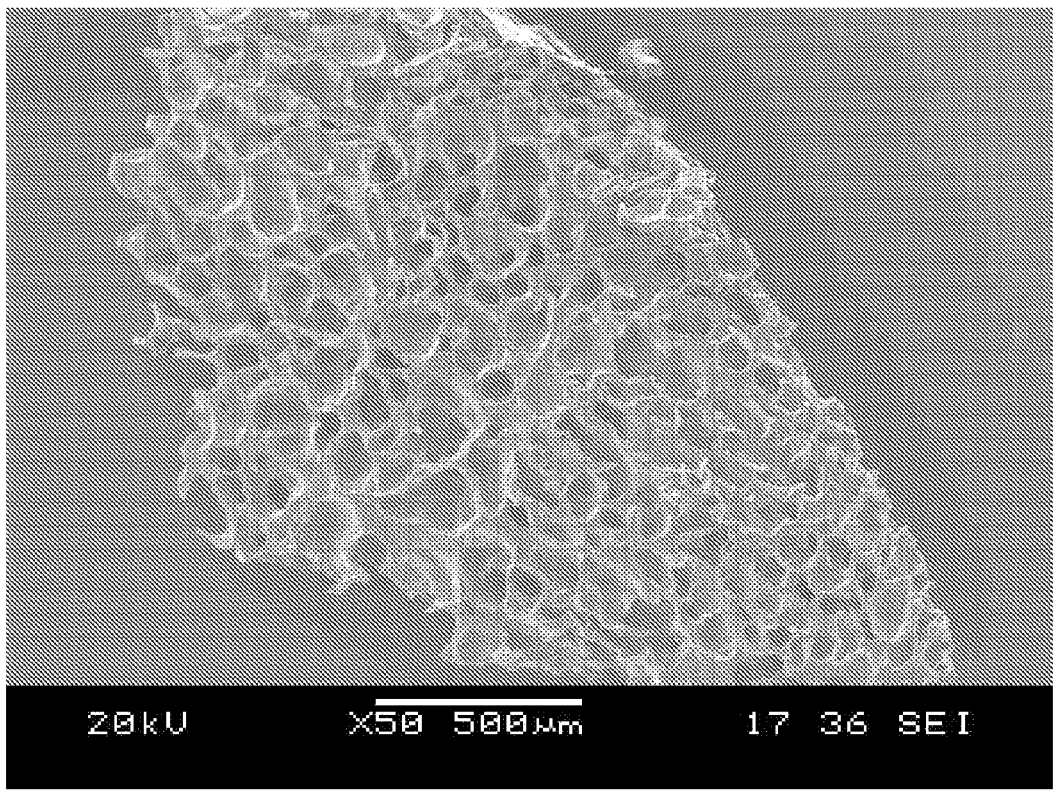
FIG. 1 a scanning electron micrograph (SEM) image of a section of a porous fibroin material according to the invention.

As shown in FIG. 1, the material has been seen to contain a high density of intercommunicating pores (up to 75%) with an average pore size ranging from 10 µm to 1 mm.

Testing has shown that the implantable optimised fibroin material comprises an unconfined compressive tangent modulus (stiffness) of between 0.3-5.0 MPa at 5% strain (shown in FIG. 6) and an ultimate compressive strength (stress to yield point) of 0.5 to 6 MPa Further testing of the implantable optimised fibroin material has shown and an Equilibrium Modulus of approximately 0.2 to 4.6 MPa and a Dynamic Modulus of approximately 1.5 MPa to 12 MPa over prolonged compression testing.

The optimised fibroin material has demonstrated good resilience measurable by the percentage of unrecoverable deformation of a sample. Resilience testing has shown a deformation of 6.7% after 5 cycles of loading to a 20% strain in an unconstrained test immersed in cell culture medium (shown in FIG. 3) and a deformation of 8.2% over 1.2 million cycles taken to 5N strain.

Blood assays have demonstrated low levels of pyrogenicity falling within EU guideline limits and no cytotoxicity.

The material is also slowly resorbable showing a loss of material at 12 months.

The material has also demonstrated a smooth articular surface having a low friction coefficient and a stiffer surface when compared with the underlying material.

The fibroin material is made from a regenerated fibroin solution using the protocol described below.

Overview of the Method for Preparation of Fibroin Material

The regenerated fibroin material is prepared from silk or silk cocoons. The silk is a Mulberry silk, a Wild Silk, a recombinant silk, or a combination of these silks.

The silk or silk cocoons are treated with ammonia or with an aqueous solution containing ammonium ions. In this step, it is believed that ammonium ions act as a salting in reagent, which increases the subsequent solubility of the protein in the chaotropic reagent by assisting in the removal of an inner water shell surrounding the protein chains and by binding to the charged amino acid side chains of the fibroin.

The silk or silk cocoons are dried by extracting water.

The silk or silk cocoons are degummed by selectively removing the sericin. This is done by enzymatically cutting and removing the sericin using a suitable enzyme which cleaves sericin, but produces little or no cleavage of fibroin.

The silk or silk cocoons are dissolved in one or more chaotropic agents either at a temperature of less than 60° C. and/or with a concentration of chaotropic agent of less than 9.5M and/or for a period of time of less than 24 hours.

The chaotropic agents are removed by dialysis using ultrapure water at a temperature of approximately 4° C. The resulting solution is concentrated to provide an optimized regenerated fibroin solution.

The solution is transferred to a mould for gelling, or alternatively, the solution is left in the dialysis vessel. The solution is gelled by treating the solution with an acid, for example, an acidic solution or acidic buffer or acidic vapour, although other gelling methods that are known in the art can be used.

The gelled material is then subjected to one or more freezing cycles to produce the fibroin material or scaffold. By freezing the gelled material the water droplets are turned to ice crystals which form pockets or pores within the material.

The material or scaffold can optionally be treated with an aqueous ethanol solution to increase the concentration of the beta sheet conformation of the fibroin thereby improving its mechanical properties and reducing its solubility and swelling in aqueous media.

The order of several of these steps can be varied. Particularly, the silk can be treated with ammonia gas or solutions containing ammonia or ammonium ions before or after degumming. Similarly degumming can take place before, or after reeling silk from cocoons.

Development of the Process for Preparation of the Optimized Fibroin Material

Each step in the process of preparing the porous fibroin material has been subjected to optimization in a highly iterative procedure. These iteration processes sought the mildest possible procedure for degumming and for dissolving the silk to reduce the chance of degrading the fibroin by chain scission and reduced refolding of the protein into the native silk I-like state. The optimization of each step both singly and when used alongside changes to other steps was carried out by assessing:

1. The effect of changes on the reduction in the gelling time of drops of aqueous 5-8% w/v fibroin solutions when exposed to glacial acetic acid vapour at 20° C.; and
2. The stiffness of the final porous material.

Treatment with Ammonia, or Ammonium Ions

It was discovered that treatment of the silk with ammonia gas, or a dilute solution of ammonia or an ammonium salt greatly increased the readiness of silk to dissolve in a lithium bromide solution or other chaotropic agent. It is thought that treatment with ammonia or ammonium ions leads to an increase in the solubility of the protein by the "salting in" effect and the binding of the ions to the protein.

It was found that this treatment was effective when applied at one or all of three stages: directly to undegummed cocoons; to raw silk fibres, to degummed or partially degummed silk whether degummed by conventional industrial degumming methods or by enzymatic degumming. Ammonia or ammonium ions were also effective when included as a component of the buffer used for enzymic degumming. Thus any of these methods of treatment of silk with ammonia or ammonium ions could be used to reduce the temperature, or the time, or the concentration of the chaotropic agent required to dissolve the silk resulting in reduced damage to the fibroin and a saving in process costs.

Treating $B.$ $mori$ silk with ammonia or ammonium ions enabled the time for dissolving the silk in 9.3 M lithium bromide solution at 60° C. to be cut from several hours to 15 minutes. Alternatively, ammonia or ammonium ion treatment enabled 7M lithium bromide to be used in place of 9.3 M at 60° C. It also enabled the silk to be completely dissolved in 9.3M lithium bromide solution at 20° C. within 24 hours. It further enabled the silk to be completely dissolved in 9.3M lithium bromide at 37° C. within 4 hours.

Therefore, it was found that treatment with ammonia or ammonium enables a range of milder treatments in which the temperature, concentration of the chaotropic agent or time required for solution can be varied singly or in combination. These milder treatments resulted in more rapid gelling times for the fibroin solution and stronger stiffer materials at the end of the process.

It is currently considered that another pair of ions with the same size, for example, potassium chloride will also have the same effect and could be used in place of the ammonia. This is supported by two lines of evidence: (1) The Jones-Dole viscosity (a measure of the chaotropicity) of potassium and chloride ions are similar as is the charge density enabling the ions to form ion pairs and help to remove an inner water shell of the protein (properties shared with ammonium chloride; and (2) Potassium chloride has been used to "salt in" proteins at salt concentrations generally ranging from 50 mM to 600 mM.

It is currently considered that certain other ionic reagents comprising an aqueous solution of monovalent cations and monovalent anions could provide the same effect. Particularly, it is thought that an ionic reagent comprising monovalent cations and monovalent anions having ionic radii of at least 1.3 Angstroms and a Jones-Dole B coefficient of between −0.05 and +0.1 at 25° C., would provide the same effect as the described in relation to the ammonium ions.

Suitable ionic reagents may include aqueous solutions of ammonium hydroxide, ammonium chloride, ammonium bromide, ammonium nitrate, potassium hydroxide, potassium chloride, potassium bromide and potassium nitrate.

Drying

The silk or silk cocoons are air dried overnight at room temperature in less than 20% humidity and in the presence of anhydrous calcium chloride.

The removal of substantially all of the water through drying increased the concentration of the ions in the solution, which was thought to enhance the effects of the ions and the resultant material.

Other known methods of drying such as freeze drying and drying through the application of heat would achieve the same effect. If heat drying is used, a temperature of less that 100° C. is thought to result in an improved fibroin material.

Degumming

The choice of the degumming method was also found to be crucial for the gelling time of the fibroin and stiffness and strength of the final material. Commercial reeling and degumming processes both use temperatures of around 100° C. and the use of sodium carbonate and/or Marseille's soap and it was found that reeled raw silks and degummed silks dissolved less readily than cocoon silks probably as a consequence of this treatment.

Degumming with commercial alcalase (bacterial subtilisin) enabled the degumming temperature to be reduced to 60° C. Alcalase is a member of the Serine S8 endoproteinase family and is likely to degrade fibroins badly as it has a broad specificity with a preference for a large uncharged residue in the P1 position. *B. mori* and *Antheraea pernyi* heavy chain fibroins have many predicted cleavage sites for this enzyme. The susceptibility of *B. mori* fibroin to alcalase cleavage was confirmed by polyacrylamide gel electrophoresis of a regenerated fibroin solution prepared from alcalase degummed silk.

In the case of degumming using trypsin the temperature for degumming could be reduced to 20-40° C. and gave gels with reduced gelling times, and with improved stiffness and strength compared with conventional high temperature degumming procedures. In contrast to alcalase, the tool PeptideCleaver showed few predicted trypsin cleavage sites in the consensus sequence of the repetitive crystalline domains and of the hydrophilic spacers of *B. mori* fibroin heavy chain fibroin and none in the consensus sequence or hydrophilic spacer in *A. pernyi* heavy chain fibroin. This suggested that it might be beneficial to degum silks in trypsin for the preparation of regenerated silk solutions. Trypsin was indeed found to be highly advantageous for degumming silk for the formation of improved regenerated silk solutions.

Silks degummed with trypsin gave regenerated silk solutions with shorter gelation times and capable of forming stiffer hydrogels than those obtained from regenerated silk prepared from silk degummed with alcalase. Degumming with trypsin gave gelling times of less than 5 minutes on exposure to glacial acetic acid vapour and also gave the stiffest and strongest materials suggesting that trypsin under these conditions produced much less chain cleavage than alcalase treatment.

It will be understood that other proteolytic enzymes producing little or no cleavage of fibroin may also be advantageous for degumming silks for the preparation of improved regenerated fibroin solutions. The observation that *B. mori* heavy chain fibroin contains very little proline while this amino acid is relatively abundant in sericin suggested that proline endopeptidase would be an ideal candidate to selectively remove sericin while producing little or no damage to fibroin.

Dialysis

In the course of these iterations it was found to be highly beneficial to dialyse regenerated fibroin solutions against type I milliQ™ water (available from Millipore™, 290 Concord Road, Billerica, Mass. 01821, US) otherwise known as ultrapure water, to remove the chaotropic agent from the silk solution.

It was noted that PIPES or Tris buffers or impurities in deionised water adversely affected the stiffness and strength of the final product when used as dialysants. It was noted that the inclusion of PIPES or Tris buffers or impurities in the dialysant also increased the viscosity of the regenerated silk solution probably as a result of their ability to encourage the aggregation of the fibroin chains by binding to them and this is thought to be disadvantageous in the formation of strong and stiff fibroin gels.

It is considered that it may be of further advantage to use cocoon or raw silks degummed with trypsin in ammonium carbonate buffer at 40° C.

Gelling

The optimised regenerated fibroin solution was gelled by exposure to an acetic acid solution, or an acidic buffer or to acetic acid vapour. The concentration of the acidic buffer and length of exposure to it were crucial to the pore size and the strength and stiffness of the resulting gel. Too concentrated acetic acid solutions or prolonged exposure to acidic buffers resulted in over-gelation of the fibroin.

Freezing under-gelled fibroin resulted in a reduction in the pore size and weaker scaffolds while strong over-gelation gave non-porous gels containing a low density of large splits produced by large ice crystals. It was found that the length of exposure and concentration of the acidic buffer or vapour required for optimal gelation depended on the geometry and size of the fibroin cast. Thus longer treatments were required to optimally gel fibroin in moulds constructed from 20 mm diameter dialysis tubing compared with 10 mm dialysis tubes.

It was found to be advantageous to gel 8-10% w/v optimised regenerated silk fibroin solution prepared from trypsin degummed silk contained in 10 mm diameter dialysis tubes for 2.5 hours to 5 hours with aqueous 1% w/v acetic acid at 20° C. In contrast similar solutions prepared from alcalase degummed silk required gellation for 16 hours under the same conditions. The greatly extended treatment time for alcalase, compared with trypsin degummed silk probably results from much greater degradation of the fibroin chains in the former (see above).

It will be understood that several agents can be used to facilitate the formation of a hydrogel from the improved regenerated silk solution. By way of example only these include acetic acid solutions, acetic acid vapour, other acidic solutions or buffers or vapours, solutions containing calcium ions, surfactants, heating, ultraviolet light, laser radiation, microwave radiation, ultrasound, low frequency vibrations, dilution of the fibroin beneath 5% w/v, concentration of the fibroin beyond 10% w/v, mechanical strain, shear forces, and extensional flow. These agents can be used singly or in combination of two or more agents.

It will be understood that compared with regenerated fibroin solutions prepared by the standard protocol disclosed in the literature, the reduced degradation of the optimised regenerated fibroin solution, its greatly shortened gelation time and its heightened sensitivity to extensional flow and shear make it highly advantageous for extrusion into strong filaments.

Compared with that prepared by the standard protocol, the optimised regenerated fibroin solution is also highly advantageous for coatings, for forming beads and microspheres, for encapsulation, as an adhesive, for casting of films, and for incorporation into composite materials.

Freezing

For the preparation of porous implantable material the optimised regenerated fibroin solution after gelling can be rendered porous by freezing. Freezing is thought to result in phase separation of a fibroin-rich phase from a fibroin-poor phase and ice crystal formation in the latter. These two mechanisms are thought to combine to give rise to a high density of interconnected pores in the gels.

The branching dendritic pattern of ice crystals formed in this way is reflected in the orientation of the approximately ellipsoidal pores and the distribution of the interconnections between the pores. The walls of these pores are strongly birefringent. The sign of the birefringence shows that the fibroin molecular chains are highly aligned circumferentially around the pore walls. This suggests that freezing strains and orientates the molecules in the pore walls. It will be understood that the orientation of the fibroin obtained in this way contributes beneficially to the mechanical properties of the material.

The freezing step also makes the fibroin in the pore walls insoluble in water and most other aqueous solvents suggesting that it has been partially converted to the insoluble silk II state in which intra- and inter-molecularly bonded beta-sheets predominate. This transition to the silk II state may result from the removal of water from the protein chains produced by a combination of phase separation and their alignment and pulling together, both as a consequence of ice crystal formation. Thus the formation of the insoluble silk II state rather closely mimics the natural process by which silks are extruded which also depends on phase separation, loss of water from the fibroin-rich phase and strain dependent orientation and silk II formation.

For a single freezing cycle, the temperature of the freezing step has a small effect on the pore size with the largest pores produced by freezing between −12° C. to −16° C. Varying the temperature and including low concentrations of antifreezes or sugars in the regenerated protein solution can be used to vary the ice crystal size and morphology and hence the size and shape of the pores in the material.

Increasing the number of freezing cycles produced an increase in the size of the pores as a result of damage by ice crystals. This was accompanied by some loss in the stiffness and strength of the final material.

Zone freezing gives advantageous control over the shape and orientation of the ice crystals and hence the shape and orientation of the pores. Defining the points, loci or planes at which zone freezing is initiated provides a means of controlling the branching pattern of ice crystal formation and hence the pattern of orientation of the ellipsoidal pores and the distribution of the interpore connections in the fibroin material. It will be understood that this enables porous fibroin scaffolds to be produced in which the arrangement of pore walls mimics the arrangement of extracellular materials in tissues.

Thus, for example, zone freezing a thin slab of fibroin hydrogel placed on a single cold plate lying in the plane of the future osteochondral surface gives an anisotropic branching and radiating pattern to some extent resembling the arrangement of collagen fibres in the deep layers of cartilage. It is to be understood that scaffolds mimicking the tissue plan of other tissues could be made in this way.

It will be understood that methods other than gelation and freezing can be used to introduce intercommunicating pores into the optimised regenerated fibroin solution. By way of example only these include salt leaching and gas foaming.

Treatment with Ethanol Solution

Treating the porous fibroin hydrogel with an aqueous ethanol solution after freezing, is thought to facilitate the formation of beta sheet inter and intramolecular hydrogen bonds which improve the mechanical stability of the hydrogel and increase insolubility and resistance to enzymatic attack.

The invention will now be described by way of example only in the following examples.

Example 1

Protocol for the Preparation of Regenerated Silk Fibroin Solution from Natural Fibres from Silk or Silk Cocoons 1. Freshly formed *Bombyx mori* silk cocoons or reeled raw silk were treated with 10 mM ethylenediaminetetraacetic acid (EDTA) solution for one hour at room temperature.
2. The silk cocoons or reeled raw silk was then rinsed in the same solution and thoroughly washed with ultrapure water.
3. Silk was then degummed at 30-40° C. with a trypsin solution at pH 8.5-9.3 in a buffer containing an ammonium salt or ammonia.
4. The silk was thoroughly washed in ultrapure water.
5. The water was squeezed out and the silk cocoons or reeled raw silk were treated with an aqueous 0.1 to 0.001 M ammonium chloride or ammonium hydroxide solution containing ammonium ions for 1 hour at 20° C.
6. The silk cocoons or reeled raw silk was dried overnight at room temperature in conditions of less than 20% humidity and in the presence of anhydrous calcium chloride.
7. The silk was dissolved in an aqueous 9.3M solution of lithium bromide for 4-5 hours with constant stirring at 37° C., at a ratio of 1 g of silk to 5 ml of lithium bromide solution.
8. The resulting fibroin solution was transferred to Visking tubing (molecular weight cut off 12-15 kDa) and dialysed for a minimum of 5 hours and a maximum of 3 days against ultrapure water at 5° C. with constant stirring in covered beakers. A large excess of ultrapure water was changed 5 times at evenly spaced intervals.
9. After dialysis the fibroin concentration in the regenerated silk solution was between 8-10% w/v as determined by gravimetry and/or refractometry. The concentration of the fibroin was increased by leaving the unopened dialysis tubes in a vacuum to obtain a concentration of 8-30% w/v.

Example 2

Protocol for Forming Regenerated Silk Fibroin Material from Regenerated Silk Fibroin Solution 1. After dialysis the regenerated silk tubes were gelled in the tubes or in silicone moulds with aqueous 1% w/v acetic acid at 20° C. for an optimal time which depended on the size of the dialysis tubing or mould.
2. After gelling, the dialysis membrane or mould was immediately removed to allow the gelled fibroin to expand freely during freezing.
3. Zone freezing was carried out between −12 and −16° C. to obtain the optimal pore size for cell growth (approximately 300 μm). However, to achieve smaller pores the material can be frozen at a lower temperature, whilst a larger average pore size can be obtained by subjecting the material to 1 to 10 re-freezing steps.
4. While frozen, the material was optionally treated with aqueous 50%-70% v/v methanol-free ethanol at room temperature for at least 30 minutes.

The resultant material can be safely stored in ethanol or freeze dried.

Example 3

Protocol for Testing the Fibroin Material: Porosity

The size of the pores was determined by cutting 20-30 μm sections with a bench microtome. Sections were mounted in water and were examined with a light microscope fitted with a digital camera. The maximum and minimum diameter was determined for each of 25 of the elliptical pores from the centre of the material using an image analysis package and the results were averaged.

The interconnectedness of the pores was rapidly assessed by applying pressure between thumb and forefinger to material in which the pores had been completely filled with water by infiltration under vacuum. A rapid efflux of water from the entire cut surface of the material indicated a high level of interconnectedness and this was confirmed by the ingress of air after releasing the compression. Examination of thick sections of the material under a stereo microscope indicated that substantially all the pores were filled with air during this procedure. The high level of interconnection of the pores was confirmed by light microscopy of sections of the material and by scanning electron microscopy of cut or freeze-fractured surfaces of the material broken in liquid nitrogen or cut with a razor blade. The porosity of the material was high, up to 75% as measured by the percentage of the cross-sectional area occupied by voids. FIG. 1 shows a scanning electron micrograph of a section of a porous scaffold prepared according to the protocol according to the method of the present invention. The material can be seen to have a high porosity.

Example 4

Protocol for Testing the Fibroin Material: Equilibrium and Dynamic Modulus Testing A The objective of this study was to determine the effect of prolonged cyclic-compression testing on the behavior of optimised fibroin material.

Method:—

Six cylindrical samples approximately 8 mm in diameter and 3.2 mm tall were cut with a sharp cork borer and a Valentine knife from a single stock of porous, alcohol treated optimised fibroin material prepared as described above from optimised fibroin solution. To obtain consistent thickness, razors fixed 3 mm apart were driven through the cylindrical samples to acquire six uniform samples. The diameters of these plugs were verified with digital calipers and the faces of the plugs were inspected to ensure a flush interface with the platens.

A mechano-active tissue engineering (MATE) system was used for material characterization and cyclic stimulations.

The plugs were placed in the center of their respective MATE test chambers and were immersed in bovine serum albumin.

The testing protocol consisted of 100 sequences. Each sequence involved three steps:

1) measurement of material properties;
2) application of 10,000 cycles (5 N amplitude, 2 Hz, 0.1 N preload, yielding nominally 5% strain amplitude); and
3) relaxation for one hour in an unloaded state.

A total of one million cycles were applied in approximately 7 days and 20 hours.

To measure material properties, ten sinusoidal oscillations (5 Hz, 1N amplitude) were applied after the samples had relaxed for one minute at 2N of compression. The Dynamic Modulus ($M_{dyn}$) was calculated as the ratio of stress amplitude over strain amplitude during the latter 3 cycles. The samples were then compressed an additional 1N and allowed 1 minute for relaxation. The incremental ratio of stress to strain during this relaxation period was used to compute the Equilibrium Modulus ($M_{equil}$).

Results:—

The initial thickness of the samples plugs was 3.20±0.15 mm.

In four of the samples the thickness decreased by only 0.15±0.01 mm after one million cycles, with over 90% of the total deformation occurring in the first 150,000 cycles.

The average Equilibrium Modulus of the samples steadily increased during cyclic testing. Near to 600,000 cycles, the average Equilibrium Modulus began to decrease in value. Upon closer inspection, this general decrease was due to sharp reductions in Equilibrium Modulus for only two of the samples.

A similar trend was observed for the Dynamic Modulus.

Conclusions:—

Four of the samples preserved their structure and Equilibrium Modulus throughout testing. The average Equilibrium Modulus of the samples was 0.2-0.46 MPa, close to the Equilibrium Modulus measured in human articular cartilage (0.2-0.8 MPa).

The Dynamic Moduli were less sensitive to structural failure and at between 2 MPa and 12 MPa were less than physiological values (13-65 MPa).

The study was performed at room temperature and the bovine serum was not replenished during testing. Alterations to the environment may have influenced the results.

Example 5

Protocol for Testing the Fibroin Material: Equilibrium and Dynamic Modulus Testing B Method:—

Two samples of silk fibroin material with 400·m porosity were tested. The samples were app. 3 mm in height and 8 mm in diameter.

The samples were rehydrated by putting them in PBS and centrifuging 6 minutes at 600 rpm (=40 g).

The samples were exposed to three million sinusoidal load cycles. During the third million load cycles the test was interrupted after each 10,000 cycles for material evaluation. A short creep test and a dynamic test were interposed to evaluate the Equilibrium Modulus and Dynamic Modulus.

The following parameters of cyclic sinusoidal loading were used:

| Parameters of cyclic sinusoidal loading: Preload | 0.1N |
|---|---|
| Maximum load | 5N |
| Maximum Strain | app. 6% |
| Loading frequency | 5 Hz |

Results:—

Figure 7:
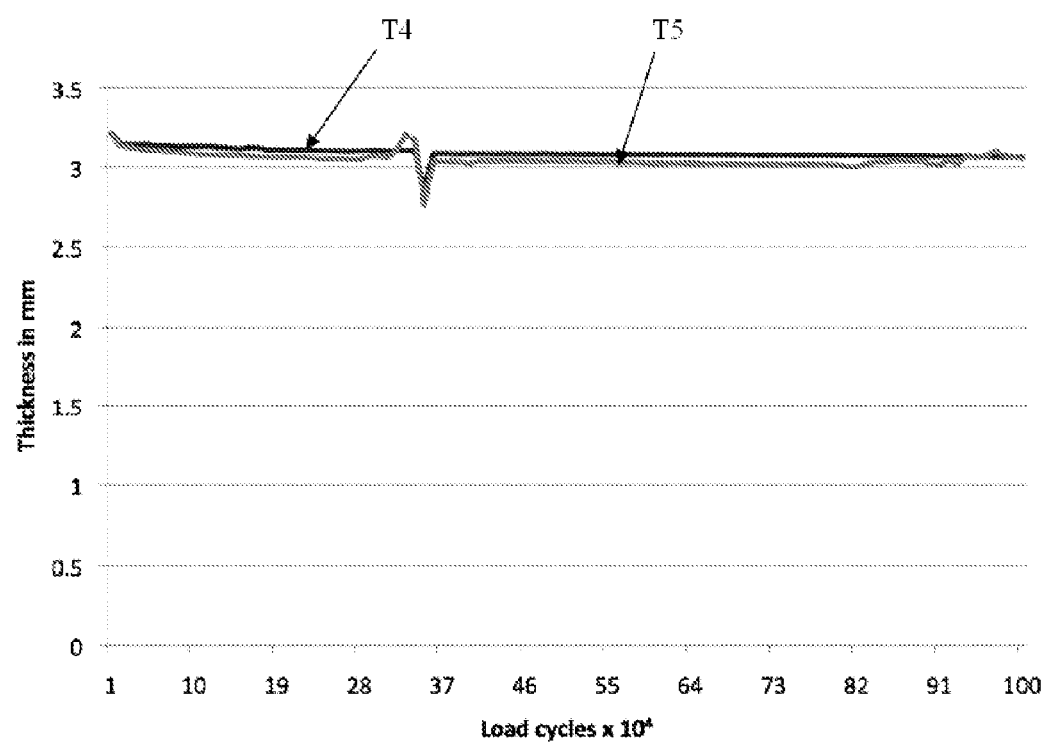
FIG. 7 a graph showing sample thickness of two tested silk fibroin material samples measured during the third million of load cycles (the curve peaks occurring at app. 350,000 load cycles were caused by measuring artefacts)

The thickness of the two tested samples slightly decreased over the last million load cycles (FIG. 7).

Figure 8:
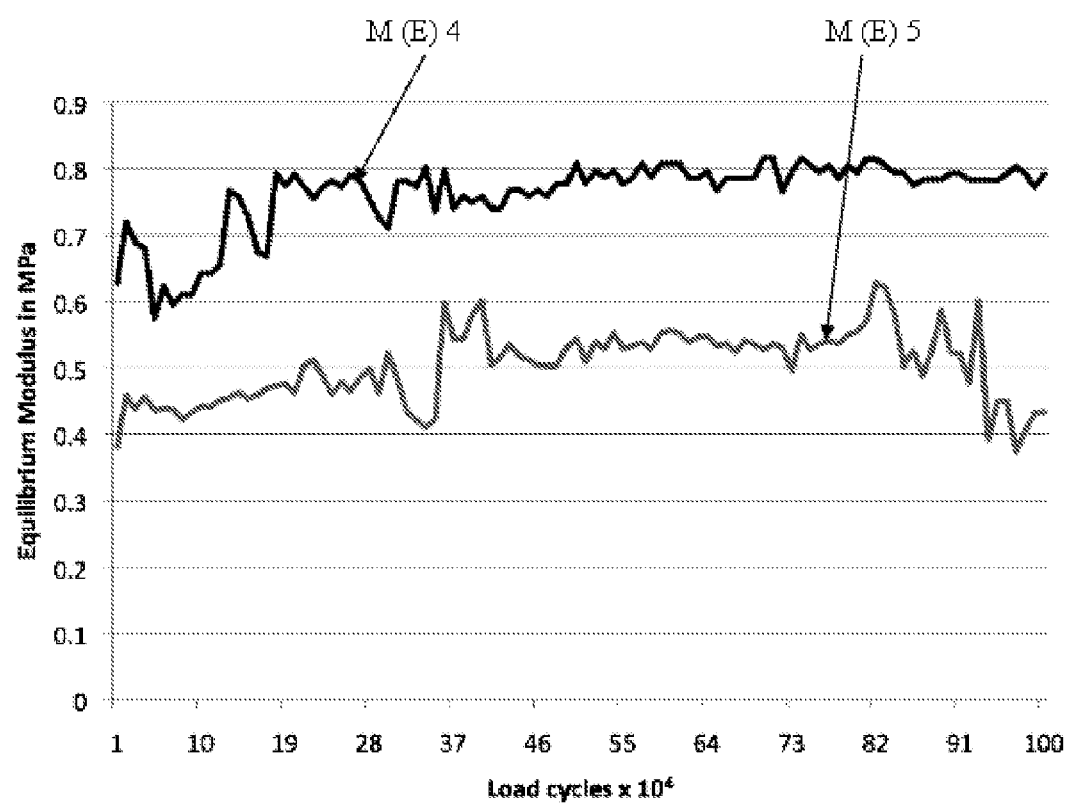
FIG. 8 a graph showing the equilibrium Modulus of two tested silk fibroin material samples measured during the third million of applied load cycles.
Figure 9:
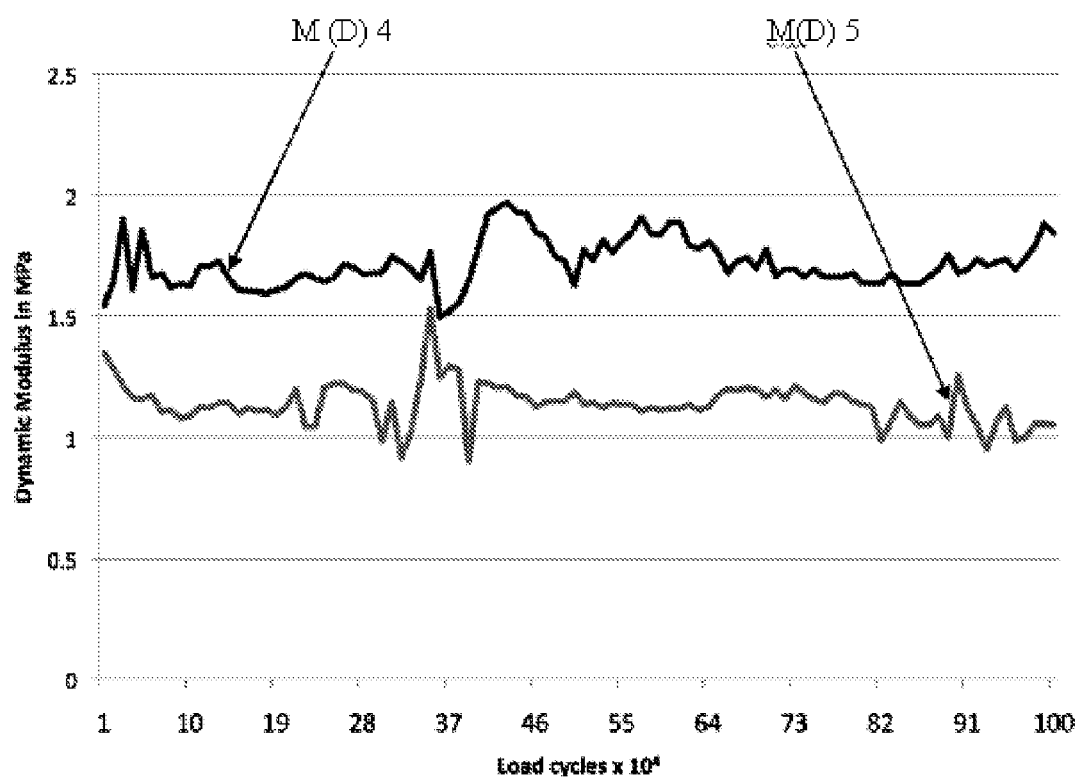
FIG. 9 a graph showing the dynamic Modulus of two tested silk fibroin material samples measured during the third million of applied load cycles.

The Equilibrium Modulus slightly increased during the testing time (FIG. 8), whilst the Dynamic Modulus almost stayed constant (FIG. 9).

Conclusions:—

The two tested silk fibroin samples did not show substantial loss of both elastic ($M_{equi}$) and viscous ($M_{dyn}$) properties over the course of the third one million load cycles after preconditioning the samples with 2 million load cycles.

Example 6

Protocol for Testing the Fibroin Material: Resilience Testing A

Method 1:—

The samples, measuring 8 mm diameter by 10 mm depth, were compressed to 20% strain and the stress-strain characteristics were plotted. All the specimens exhibited a tri-phasic response, characterised by a toe-in region, an initial linear region, followed by a reduction in gradient and a second linear region. The 15% tangent modulus corresponds to the second linear region while the 5% tangent moduli on the initial linear phase is generally a lot greater.

Results 1:—

Figure 6:
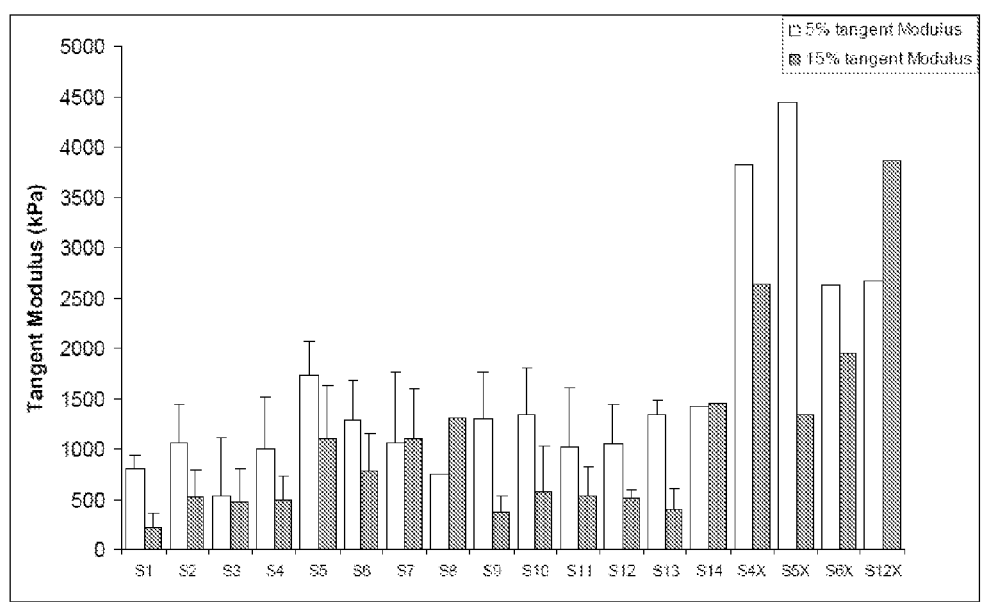

FIG. 6 shows the results of testing of 18 samples of the fibroin material. The samples suffixed with an 'X' were cross-linked using hexamethylenedi-isocyanate. The 15% tangent moduli vary from 0.2 MPa to nearly 4 MPa, with some of the constructs having an irregular cross section, which may contribute to variability. The cross-linked (X) samples were considerably stiffer, exhibiting 5% and 15% tangent moduli of 4 MPa in some samples.

Method 2:—

One of the above samples (S6) of the optimised fibroin material was subjected to a much larger strain (20%) for five cycles of compression/relaxation with each cycle having a duration of 2.0 minutes. S6 had an average pore size of approximately 200·m and average porosity of approximately 70%. The sample was taken to 20% strain in an Instron compression testing rig.

Results 2:—

Figure 3:
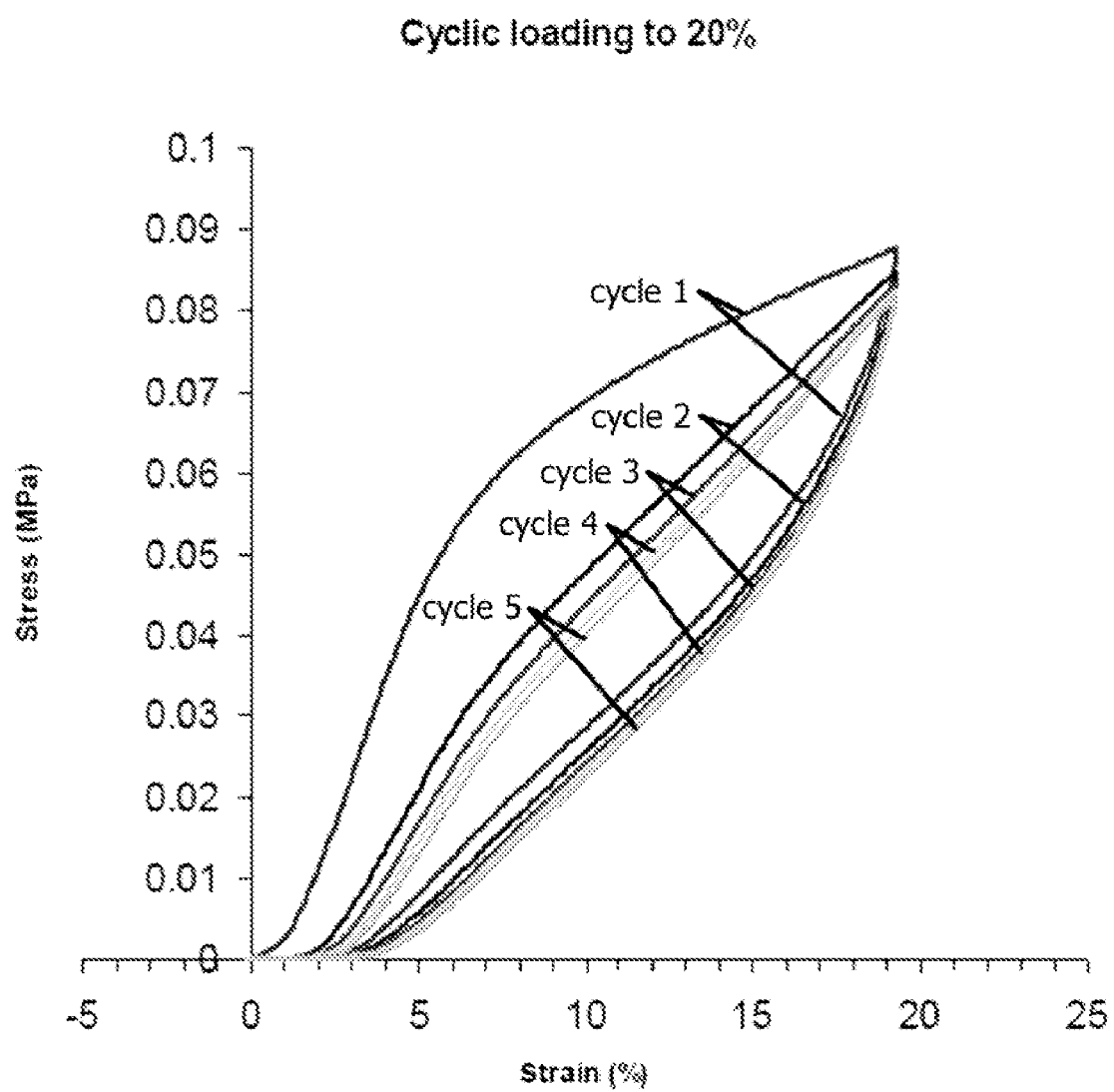
FIG. 3 a hysteresis plot showing the percentage of unrecoverable deformation of a sample of a fibroin material according to the invention after 5 cycles of loading to a nominal 20% strain in an unconstrained test immersed in cell culture medium.

FIG. 3 shows a hysteresis plot of the results:—on each cycle, the upper line shows the loading profile, while the lower line of the same cycle indicates the relaxation profile of the material once the load has been removed. The plot suggests that the first load cycle stiffens the construct by approximately 0.5 MPa (15% tangent modulus) and thereafter in subsequent cycles the specimens appear stiffer (i.e. with a 15% higher tangent modulus).

There is a very small deformation of 3.4% in the first load cycle associated with probable pore compaction and a further 3.3% over the subsequent second to fifth load cycles (the permanent deformation decreasing in percentage terms with each subsequent cycle).

Conclusion:—

This data demonstrates the resilience of the material as measured by the low percentage irrecoverable stress deformation in subsequent cycles after the first load cycle.

Example 7

Protocol for Testing the Fibroin Material: Resilience Testing B

Method:—

The Mechano-activated tissue engineering (MATE) system was used to analyse six samples of optimised fibroin material measuring 8 mm×4 mm.

The samples were not cross-linked and had an average pore size of 200 μm. Neither were the samples seeded with cells and the mechanical behaviour only of the empty samples was examined.

The samples had been dehydrated for storage and were rehydrated in Phosphate Buffered Saline (PBS) without problem by centrifugation in the medium.

Rehydrated samples were analysed over a period of 5 days using a loading regimen as follows: cycle rate: 3 Hz, force amplitude: 5 N minus a preload of 0.2 N, temperature: 37°, medium, PBS.

Results:—

After 1,200,000 cycles no indication of material degradation was observed and the material of the samples appeared structurally similar to the beginning of the experiment. Measurement of the samples revealed that the material thickness had decreased on average by 8.2% (from 3.88 mm to 3.57 mm).

Example 8

Protocol for Testing the Regenerated Silk Fibroin Solution: Gelation Time

Method:—

Drops of regenerated silk fibroin solution with a concentration of about 8% w/v were placed in the bottom of a plastic petridish and were exposed to vapour at room temperature from a drop of glacial acetic acid placed on a filter paper in the lid of the dish. To establish the gelation time the drop was probed with a plastic Eppendorf pipette tip. The material was deemed to have gelled when it would no longer flow when the dish was tilted or when probing the surface of the drop produced an irrecoverable deformation in the surface of the drop.

To compare the gelation time of the optimised regenerated fibroin solution directly with the fibroin solution disclosed in US2007/0187862, the protocol described therein was replicated.

The pH of the optimised regenerated fibroin solution containing 8% w/v fibroin was adjusted to pH 6.5-6.8 using very dilute hydrochloric acid or sodium hydroxide solutions and the concentration determined by refractometry using a calibration curve prepared from over 100 samples of optimised dialysed fibroin solution whose fibroin concentration had been determined by gravimetry. 0.5 ml aliquots of this solution were transferred to small cylindrical glass tubes with an internal diameter of 10 mm which were sealed with parafilm. The tubes were incubated either 60° C. and inspected regularly. The time taken for the material to cease to flow when the tubes were inverted was determined.

FIG. 7 in US2007/0187862 gives an average gelation time of 4 days at 60° C.

Results:—

The gelling time for the optimised silk fibroin measured in this way was 5 hours. Thus the gelation time for the optimised regenerated fibroin solution reported herein is approximately 20 times faster than for the silk fibroin solution reported in US2007/0187862. This taken together with the evidence from rheological testing described demonstrates the superiority of the optimised regenerated fibroin solution over that disclosed in US2007/0187862.

Example 9

Protocol for Testing the Regenerated Silk Fibroin Solution: Liquid Crystallinity Method:—

To investigate whether the regenerated silk fibroin solution could form a liquid crystalline mesophase, droplets of the approximately 8% w/v optimised regenerated fibroin solution were placed on glass slides with or without coverslips and with or without adjustment to pH 6.5 with 0.1 M ammonium acetate buffer. Slides were allowed to dry slowly at 4° C. by placing the slide in a plastic Petri dish with a lid. Under these conditions small spherulitic crystals of fibroin slowly formed in the fibroin.

Results:—

Figure 2:
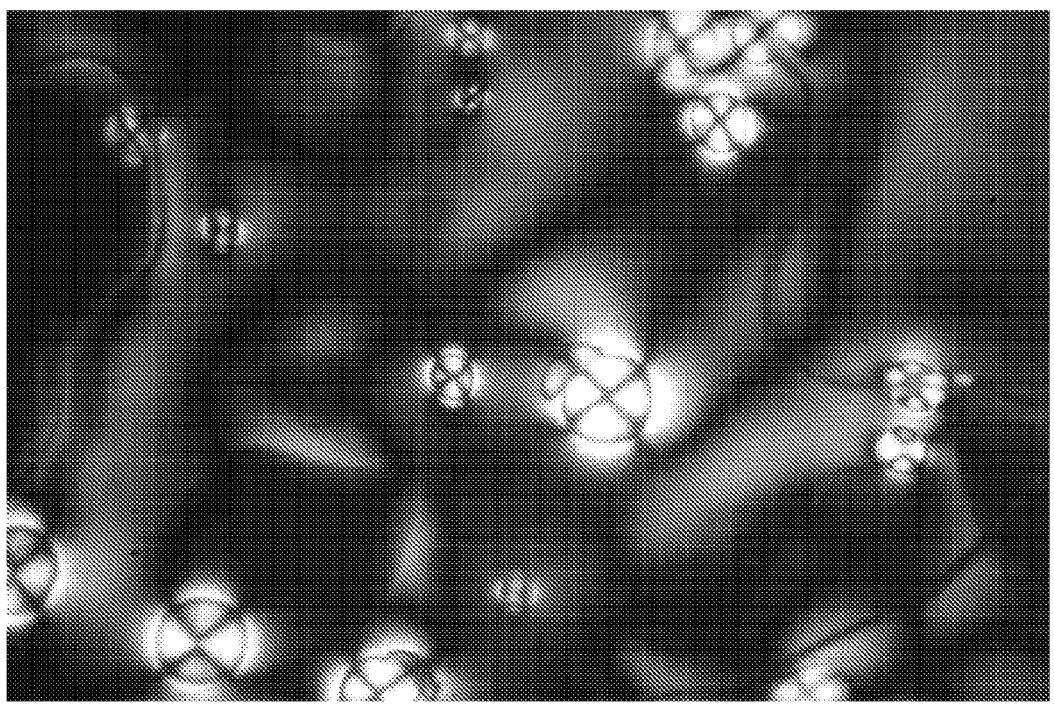
FIG. 2 a polarizing microscope image of a sample of a fibroin solution according to the invention showing the formation of small spherulitic crystals of fibroin.

As shown in FIG. 2, when examined under the polarizing microscope most of the samples showed a maltese cross pattern with four radial isogyres. The liquid phase surrounding the spherulites showed a pattern of irregularly curved isogyres, some of which are continuous at their origin with the isogyres of the spherulites indicating a calamitic liquid crystalline phase. The largest spherulite in the micrograph has a diameter of 10 μm.

This indicates that, like native silk fibroin in, or taken from, the silkworms silk gland, the optimised regenerated silk fibroin solution is capable of forming a calamitic liquid crystalline mesophase. This effect is not seen in regenerated silk solutions prepared by the standard protocol described in the literature. These observations demonstrate that the optimised regenerated silk fibroin prepared according to the protocol of the invention closely resembles native silk fibroin taken directly from the silk gland in the animal and is superior to that prepared by the conventional process described in the literature. It will be appreciated that the ability to form a mesophase is important for allowing the fibroin molecules to be readily orientated in the pore walls during the freezing step.

Example 10

Protocol for Testing the Regenerated Silk Fibroin Solution: Rheological Testing

Rheometry was used to investigate whether samples of the optimised regenerated silk fibroin solution had rheological properties close to that of native silk fibroin and very different from that of regenerated silk fibroin prepared by the standard protocol disclosed in the literature. The protocol for investigating the rheology of silk fibroin solutions is described below.

Method:—

A Bohlin Gemini 200 HR Nano rheometer (torque range 10 nNm to 200 mNm, controlled stress/rate viscometry, 3 nNm to 200 mNm, controlled stress/strain oscillation, Malvern Instruments, UK) was used with a cone and plate CP 1/10 (D=10 mm 1° incline). An environmental cuff with moistened tissue was used to prevent the sample drying out. A temperature control unit (Bohlin KTB 30, Malvern Instruments, UK) was used to maintain the temperature at 25° C. Samples were loaded onto the lower plate of the rheometers taking care not to strain the viscous solutions. Optimised regenerated silk fibroin solution was compared with native silk protein obtained directly from the middle division of the final instar *Bombyx mori* silk gland and regenerated silk solutions prepared using the standard protocol described in the literature (see above). All samples had a concentration of approximately 20±1% w/v as determined by gravimetry. To reach this value regenerated silk solutions in dialysis tubes were concentrated by vacuum evaporation at room temperature.

Results:—

Figure 4:
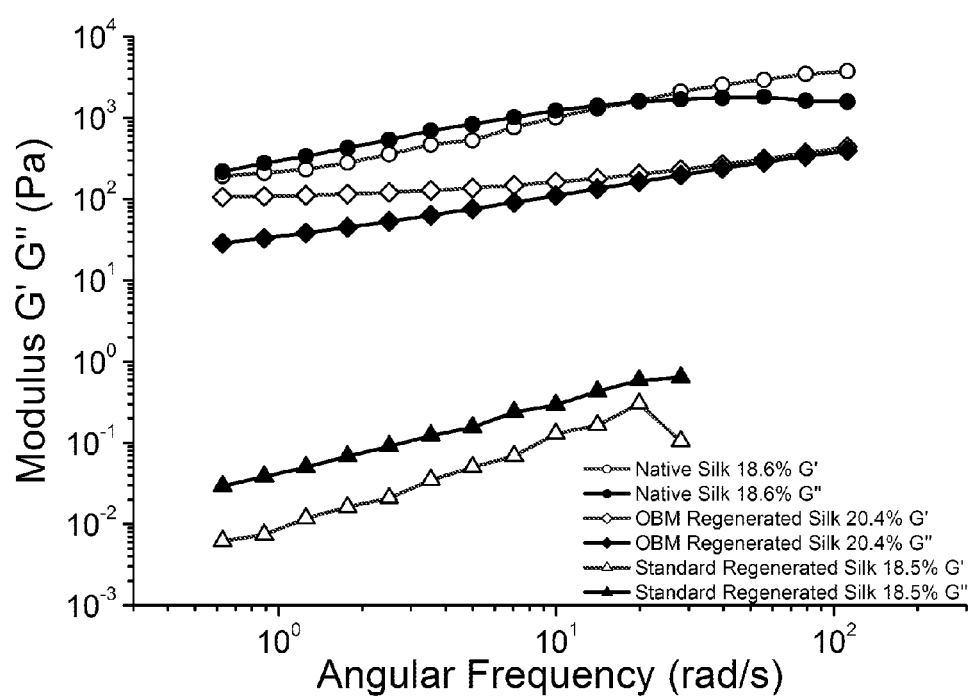
FIG. 4 a graph showing a comparison of the storage moduli of regenerated fibroin according to the invention, regenerated fibroin according to the standard protocol, and native silk protein taken directly from the silk gland.

FIG. 4 shows a comparison of the storage moduli of optimised (OBM) regenerated silk fibroin and native silk protein taken directly from the silk gland and standard regenerated silk. The G' and G" of the optimised regenerated silk fibroin are very close to those of native silk and very different from those of standard regenerated silk fibroin. These parameters for the optimised (OBM) regenerated silk fibroin solution are approximately three orders of magnitude better than the same parameters for regenerated silk fibroin produced through the standard protocol.

Figure 5:
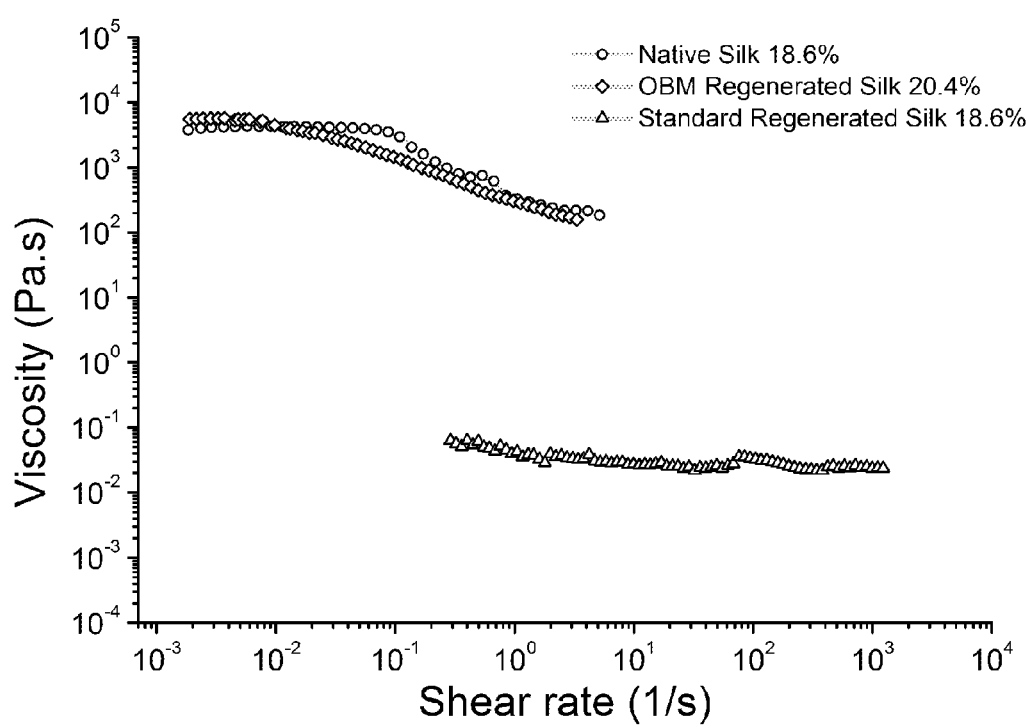
FIG. 5 a graph showing the comparison of the effect of shear rate on viscosity on regenerated fibroin solution according to the invention, regenerated fibroin according to the standard protocol and native silk protein taken directly from the silk gland FIG. 6 a graph showing 5% and 15% tangent moduli of 18 samples of fibroin material according to the invention.

FIG. 5 shows a comparison of the effect of shear rate on viscosity of optimised (OBM) regenerated silk fibroin and native silk protein taken directly from the silk gland and standard regenerated silk. The behaviour of the optimised regenerated silk fibroin solution (OBM Regenerated silk) is closely similar to that of native silk fibroin solution at the same approximate concentration while the viscosity for a shear rate of 1/s is approximately 4 orders of magnitude higher than that of regenerated silk fibroin produced through the standard protocol.

Conclusion:—

FIGS. 4 and 5 show that the rheology of the optimised regenerated fibroin solution was closely similar to that of native silk fibroin at the same concentration (approximately 20% w/v) and markedly different from that of regenerated silk fibroin prepared by the standard protocol. These rheological observations clearly demonstrate the vast superiority of the material compared with that prepared using the standard protocol.

Example 11

Protocol for Testing the Regenerated Silk Fibroin Material: Pyrogenicity and Cytotoxicity Whole blood assays were performed to assess the pyrogenic activity of samples of the fibroin material.

The blood assays tested the reactivity of IL-1·, TNF· and IL-8.

Data obtained from profiling IL-1β indicate low levels of pyrogenicity for most of the tested materials, within EU guideline limits. TNF-· and IL-8 measurement gave almost identical results to the IL-1β measurement.

In conclusion, the results of the tests showed that the samples have low pyrogenicity and display no cytotoxicity.

With the method of the present invention, the resultant implantable material is capable of carrying out the mechanical functions of meniscal, intervertebral or articular cartilage from the moment of implantation. The high and open porosity combined with resilience enables the material to draw up mesenchymal cells whether these are seeded into the material ex corpore or released into the synovial cavity or space between two vertebral centra after implantation of the material. The excellent biocompatibility and adhesiveness for cells allows them to adhere, grow and differentiate within the pores of the material. Further the material combines high toughness and resilience with slow and tunable resorbability. This enables the material to survive repeated load cycles in situ while mechanical stimulation from normal movements and/or physiotherapy encourages the cells to form new functional tissue with mechanical properties appropriate to and dictated by the local load regime as will be understood by a person skilled in the art. Finally, the smooth and stiff and tough surface of the material provides a low friction surface when lubricated with synovial fluid.

Although a few preferred embodiments have been shown and described, it will be appreciated by those skilled in the art that various changes and modifications might be made without departing from the scope of the invention, as defined in the appended claims.

It is of course to be understood that the invention is not intended to be restricted to the details of the above embodiments which are described by way of example only.

The invention claimed is:

1. A method of preparing a regenerated fibroin solution, the method comprising the steps of:
   (a) treating the silk or silk with an ionic reagent comprising aqueous solutions of one or more of ammonium hydroxide, ammonium chloride, ammonium bromide, ammonium nitrate, potassium hydroxide, potassium chloride, potassium bromide and potassium nitrate;
   (b) subsequently drying the silk or silk cocoons after treatment of the silk or silk cocoons with the ionic reagent; and
   (c) subsequently dissolving the silk or silk cocoons in a chaotropic agent.

2. The method according to claim 1, wherein the step of dissolving the silk or silk cocoons is performed under any one of the following conditions, or any combination of the following conditions:
   at a temperature of less than 60° C.;
   with a concentration of chaotropic agent less than 9M; and
   for a period of time of less than 24 hours.

3. The method according to claim 1, wherein the method comprises a further step of degumming the silk or silk cocoons.

4. The method according to claim 1, wherein substantially all of the water is removed from the treated silk or silk cocoons.

5. The method according to claim 3, wherein the degummed silk or silk cocoons are dissolved in the chaotropic agent within a temperature range of approximately 10° C. to approximately 60° C.

6. The method according to claim 1, wherein suitable chaotropic agents include lithium bromide, lithium thiocyanate, or guanidinium thiocyanate.

7. The method according to claim 3, wherein degumming the silk or silk cocoons comprises the selective removal of sericin from the silk or silk cocoons and using a proteolytic enzyme which cleaves sericin, but produces little or no cleavage of fibroin.

8. The method according to claim 1, wherein the chaotropic agent is removed by dialysis to provide a regenerated silk fibroin solution.

9. The method according to claim 8, wherein the method comprises the step of concentrating the regenerated silk fibroin solution to a concentration of approximately 5-25% w/v.

* * * * *